United States Patent [19]
Fritze et al.

[11] Patent Number: 5,807,936
[45] Date of Patent: Sep. 15, 1998

[54] TRANSITION METAL COMPOUND

[75] Inventors: Cornelia Fritze, Frankfurt; Hans-Friedrich Herrmann, Dornheim; Gerhard Erker; Johannes Ruwwe, both of Münster, all of Germany

[73] Assignee: Targor GmbH, Germany

[21] Appl. No.: 662,040

[22] Filed: Jun. 12, 1996

[30] Foreign Application Priority Data

Jun. 12, 1995 [DE] Germany ............ 195 21 335.1
Jul. 12, 1995 [DE] Germany ............ 195 25 125.3

[51] Int. Cl.$^6$ ............................. C08F 4/64
[52] U.S. Cl. ............ 526/126; 526/134; 526/160; 526/943; 526/170; 502/152; 556/7; 556/11; 556/53
[58] Field of Search ............... 526/134, 126, 526/943; 556/7, 11, 53; 502/152

[56] References Cited

U.S. PATENT DOCUMENTS

| | | | |
|---|---|---|---|
| 5,145,819 | 9/1992 | Winter et al. | 502/117 |
| 5,153,157 | 10/1992 | Hlatky et al. | |
| 5,189,192 | 2/1993 | LaPointe et al. | |
| 5,198,401 | 3/1993 | Turner et al. | |
| 5,504,232 | 4/1996 | Winter et al. | 556/7 |
| 5,539,068 | 7/1996 | Devore et al. | 526/126 |
| 5,561,092 | 10/1996 | Ewen et al. | |
| 5,585,509 | 12/1996 | Langhauser et al. | 556/11 |
| 5,650,528 | 7/1997 | Frey et al. | 556/22 |

FOREIGN PATENT DOCUMENTS

| | | |
|---|---|---|
| 2072058 | 12/1992 | Canada . |
| 0 277 003 | 8/1988 | European Pat. Off. . |
| 0 277 004 | 8/1988 | European Pat. Off. . |
| 0 427 697 | 5/1991 | European Pat. Off. . |
| A-468537 | 1/1992 | European Pat. Off. . |
| 520732 | 6/1992 | European Pat. Off. . |
| 0 495 375 | 7/1992 | European Pat. Off. . |
| A-540108 | 5/1993 | European Pat. Off. . |
| 558158 | 9/1993 | European Pat. Off. . |
| A-582 195 | 2/1994 | European Pat. Off. . |
| A-587143 | 3/1994 | European Pat. Off. . |
| A-670325 | 9/1995 | European Pat. Off. . |
| 91/14713 | 10/1991 | WIPO . |
| WO-A-9506071 | 3/1995 | WIPO . |
| WO-A-9600734 | 1/1996 | WIPO . |
| WO-A-9613529 | 5/1996 | WIPO . |

OTHER PUBLICATIONS

John A. Ewen, 1297b Macromolecular Symposia, "Symmetrical and Lopsided Zirconocene Pro–Catalysts", vol. 89, pp. 181–196, (1995).

A. D. Horton, 6184 Trends in Polymer Science, "Metallocene Catalysis: Polymers by Design?", vol. 2, No. 5, pp. 158–166 (May 1994).

P. Zdunneck et. al, "Über Die Reaktion Von Tetramethyltitan Mit Triphenylbor Und Tribenzylbor", J. Organomet. Chem. 1970, 22, pp. 659–663.

Xinmin Yang et al., "Cation–like Homogeneous Olefin Polymerization Catalysts Based Upon Zirconocene Alkyls and Tris(pentafluorophenyl)borane", J. Am. Chem. Soc. 1991, 113, pp. 3623–3635.

Holger Braunschweig et al., "Zur Addition von Alkyldichloroboranen an Bis(n$^5$–cyclopentadienyl)dihydridowolfram", Chem. Ber. 1994, 127, pp. 1613–1614.

G. Erker et al. (1991) Chem. Ber. *124*, 1301–1310.

*Primary Examiner*—Mark Nagumo
*Attorney, Agent, or Firm*—Connolly & Hutz

[57] ABSTRACT

The present invention relates to a transition metal compound of the formula I $$L_n(X_mA_tR^1_q)_sMY_r \qquad (I),$$

where

M is a metal atom of group IIIb, IVb, Vb or VIb of the Periodic Table of the Elements, L are identical or different and are each a π-ligand or an electron donor, n is 1, 2, 3 or 4, Y are identical or different and are each a hydrogen atom, a halogen atom or an 1-dentate $C_1$–$C_{40}$-group, where l is 1, 2, 3 or 4, r is 0, 1, 2, 3, 4 or 5, and at least one of the radicals L bears at least one group $X_mA_tR^1_q$, where X are identical or different and are each a hetero atom or a $C_1$–$C_{40}$-group, m is 0 or 1, A is an atom of group IIIa, Va or VIa of the Periodic Table of the Elements, t is 1, $R^1$ are identical or different and are each a $C_1$–$C_{40}$-group, q is 1, 2, 3, 4 or 5 and s is an integer from 1 to 20.

The transition metal compound of the invention is suitable as a catalyst component for olefin polymerization.

19 Claims, No Drawings

TRANSITION METAL COMPOUND

The present invention relates to a transition metal compound which can be advantageously used for the polymerization of olefins. This compound enables the use of cocatalysts such as aluminoxanes to be omitted.

The role of cationic 14-electron complexes of the formula $R_3M^+$ (M=Ti, Zr, Hf) in the Ziegler-Natta-Polymerization using metallocenes is generally recognized (M. Bochmann, Nachr. Chem. Lab. Techn. 1993, 41, 1220).

While methylaluminoxane (MAO), as hitherto most effective catalyst, has to be used in a high excess, the synthesis of cationic alkyl complexes of the formula $R_3M^+$ (M=Ti, Zr, Hf) opens up a route to MAO-free catalysts having sometimes comparable activity.

Cationic alkyl complexes can be prepared by
a) oxidation of metallocene-alkyl complexes using, for example, $AgBPh_4$ or $[Cp_2Fe][BPh_4]$,
b) by protolysis of metallocene-alkyl compounds using, for example, weakly acid ammonium salts of the very stable, non-basic tetra(pentafluorophenyl)borate anion (e.g. $[PhMe_2NH]^+[B(C_6F_5)_4]^-$) or by
c) abstraction of an alkyl group from metallocene-alkyl compounds by means of strong Lewis acids. Lewis acids which can be used here are salts ($Ph_3C^+BR_4^-$) or strong uncharged Lewis acids such as $B(C_6F_5)_3$. J. Organomet. Chem. 1970, 22, 659 describes a reaction of $(CH_3)_5CpTi(CH_3)^3$ with triphenylborane or tribenzylborane.

J. Am. Chem. Soc. 1991, 113, 3623 describes the synthesis of "cation-like" metallocene polymerization catalysts which are prepared by alkyl-abstraction from metallocene-alkyl compounds using tris(pentafluorophenyl)borane. The crystal structure of $[1,2-(CH_3)_2C_5H_3]_2ZrCH_3]^+[CH_3B(C_6F_5)_3]^-$ shows a salt-like structure with the weakly coordinating $CH_3$ group of the borate anion on the metal center.

EP 427,697 claims this synthetic principle and a corresponding catalyst system comprising an uncharged metallocene species (e.g. $Cp_2Zr(CH_3)_2$, a Lewis acid (e.g. $B(C_6F_5)_3$) and aluminum alkyls. EP 520,732 claims a process for preparing salts of the formula $LMX^+ XA^-$ according to the above described principles.

Besides these products of the acid-base adduct type, zwitterionic systems are also conceivable.

EP 558,158 claims zwitterionic catalyst systems which are prepared from metallocene-alkyl compounds and salts of the formula $[R_3NH]^+[BPh_4]^-$. In the reaction of such a salt with $((CH_3)_5Cp)_2Zr(CH_3)_2$ protolysis occurs with elimination of methane to generate an intermediate methylzirconocene cation which reacts further by C—H activation of a tetraphenylborate carbon-hydrogen bond and renewed elimination of methane to give the zwitterion $((CH_3)_5Cp)_2Zr^+$—$(m$—$C^6H_4)$—$B^-Ph_3$. The Zr atom is here covalently bonded to a carbon atom of the phenyl ring and is stabilized via an agostic hydrogen bond. According to this reaction principle, protolysis of a metallocene-alkyl species with a perfluorinated $[R_3NH]^+[B(C_6F_5)_4]^-$ salt likewise gives a cationic species in the first step, but the subsequent reaction (C—H activation) to give a zwitterionic complex (i.e. the metal atom is covalently bonded to the "former" anion) is not possible. In this reaction, metallocenes $Cp_2MR_2$ in which the alkyl radicals R are cyclically connected to one another, for example $Cp_2Zr(2,3$-dimethyl-1,3-butadiene), are also used. This gives salts of the formula $[Cp_2Zr$—$R$—$RH]^+[B(C_6F_5)_4]^-$ after protolysis.

U.S. Pat. No. 5,198,401 claims corresponding systems using dimethylanilinium salts containing perfluorinated tetraphenylborate anions. Use is here also made of metallocene $Cp_2MR_2$ in which the alkyl radicals R are cyclically connected to one another, for example $Cp_2Zr(2,3$-dimethyl-1,3-butadiene). This likewise gives salts of the formula $[Cp_2Zr$—$R$—$RH]^+[B(C_6F_5)_4]^-$ after protolysis. EP 277,003, EP 277,004, EP 495,375 and WO 91/14713 claim systems according to a similar process principle.

Chem. Ber. 1994, 127, 1613 describes the addition of an alkyldichloroborane onto bis($\eta^5$-Cp)dihydrido tungsten, which likewise leads to a zwitteranionic compound.

The processes described for preparing the cationic systems of the formula $[R_3M]^+[BR_4]^-$ (M=Ti, Zr, Hf) have the disadvantage that the cation-forming reagents ($R_3NH^+ BR_4^-$) are sometimes complicated to synthesize and expensive. In addition, there is the problem that, after protonolysis, an amine $R_3N$ is formed from the ammonium salt, which amine can, in the case of sterically unhindered metal centers, coordinate to the strongly Lewis-acid $R_3M^+$ cation (U.S. Pat. No. 5,198,401) and leads to low polymerization activities.

The zwitterionic complexes of the structure $Cp_2Zr^+$—m—$C_6H_4B^-Ph_3$ have the disadvantage that the starting compounds are expensive and complicated to synthesize and display low polymerization activity.

Cationic systems of the structure $[Cp_2MR]^+[RB(C_6F_5)_3]^-$ display, owing to the salt-like character, very high hydrolysis sensitivities and can only be used on an industrial scale to a limited extent.

It is an object of the invention to find an organometallic compound which avoids the disadvantages of the prior art.

It has now been found that this object is achieved by a specific transition metal compound.

The present invention accordingly provides a transition metal compound of the formula I $$L_n(X_mA_rR^1_q)_sMY_r \qquad (I),$$

where

M is a metal atom of group IIIb, IVb, Vb or VIb of the Periodic Table of the Elements, L are identical or different and are each a π-ligand or an electron donor, n is 1, 2, 3 or 4, Y are identical or different and are each a hydrogen atom, a halogen atom or an I-dentate $C_1$–$C_{40}$-group, where I is 1, 2, 3 or 4, r is 0, 1, 2, 3, 4 or 5, and at least one of the radicals L bears at least one group $X_mA_rR^1_q$, where X are identical or different and are each a hetero atom or a $C_1$–$C_{40}$-group, m is 0 or 1, A is an atom of group IIIa, Va or VIa of the Periodic Table of the Elements, t is 1, $R^1$ are identical or different and are each a $C_1$–$C_{40}$-group, q is 1, 2, 3, 4 or 5 and s is an integer from 1 to 20.

Two radicals L can be connected to one another via a bridge Z.

π-Ligands are preferably unsubstituted cyclopentadienyl groups or substituted cyclopentadienyl groups which, as radicals, preferably bear one or more $C_1$–$C_{30}$-hydrocarbon radicals, e.g. 2-methylcyclopentadienyl, methyl-tert-butylcyclopentadienyl, tert-butylcyclopentadienyl, isopropylcyclopentadienyl, dimethylcyclopentadienyl, trimethylethylcyclopentadienyl, 5-phenylcyclopentadienyl, diphenylcyclopentadienyl, indenyl, 2-methylindenyl, 2-ethylindenyl, 3-methylindenyl, 3-tert-butylindenyl, 2-methyl-4-phenylindenyl, 2-ethyl-4-phenylindenyl, 2-methyl-4-naphthylindenyl, 2-methyl-4-isopropylindenyl, benzoindenyl, 2-methyl-4,5-benzoindenyl, 2-methyl-α- acenaphthindenyl, 2-methyl-4,6-diisopropylindenyl, fluorenyl, 4-methylfluorenyl or 2,7-di-tert-butylfluorenyl. Particular preference is given to indenyl derivatives. The indenyl derivatives preferably bear a $C_1$–$C_{10}$-hydrocarbon radical such as $C_1$–$C_{10}$-alkyl on the five-membered ring, particularly in the 2 position, and on the six-membered ring are either unsubstituted or bear one or more $C_1$–$C_{20}$-hydrocarbon radicals such as $C_1$–$C_{10}$-alkyl, $C_6$–$C_{20}$-aryl (e.g. phenyl or naphthyl) or two or more of the $C_1$–$C_{20}$-hydrocarbon radicals form a ring system.

For the purposes of the present invention, an electron donor is an atom of group IVa, Va, VIa or VIIa of the Periodic Table of the Elements which can bear substituents such as $C_1$–$C_{30}$-hydrocarbon groups, e.g. $C_1$–$C_{20}$-alkyl or $C_6$–$C_{14}$-aryl. Preference is given to O, $NR^4_2$, $NR^4$, $NR^4_3$, $PR^4_2$, $PR^4$, $PR^4_3$, S, $P(OR^4)_2$, $P(OR^4)$, $R^4$ or Cl, where $R^4$ is a $C_1$–$C_{30}$-hydrocarbon group such as $C_1$–$C_{20}$-alkyl or $C_6$–$C_{14}$-aryl.

The bridge Z is preferably

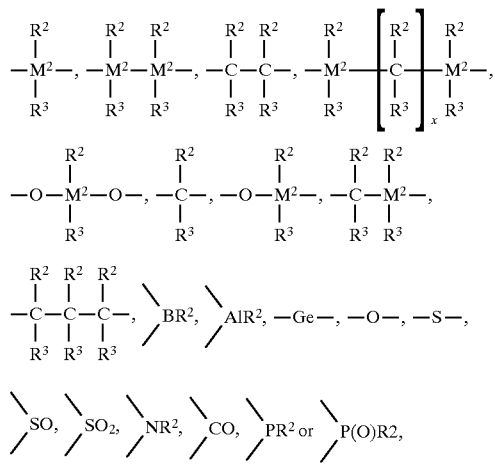

where $R^2$ and $R^3$ are identical or different and are each a hydrogen atom, a halogen atom or a $C_1$–$C_{40}$-group such as a $C_1$–$C_{20}$-alkyl group, a $C_1$–$C_{10}$-fluoroalkyl group, a $C_1$–$C_{10}$-alkoxy group, a $C_6$–$C_{14}$-aryl group, a $C_6$–$C_{10}$-fluoroaryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group or $R^2$ and $R^3$ together with the atoms connecting them form one or more rings and $R^2$ or/and $R^3$ can be bound to L, x is an integer from zero to 18, preferably 1 or 2, and $M^2$ is silicon, germanium or tin.

Z can also link two groups $L_n(X_mA_tR^1_q)_sMY_r$ with one another.

For the purposes of the present invention, a hetero atom is any atom of the Periodic Table of the Elements with the exception of carbon and hydrogen. Preference is given to silicon, germanium and tin.

The $C_1$–$C_{40}$-groups Y can be saturated or unsaturated, linear, cyclic or branched, e.g. a $C_1$–$C_{20}$-alkyl group, a $C_1$–$C_{20}$-halogenalkyl group, a $C_6$–$C_{20}$-aryl group, a $C_6$–$C_{20}$-haloaryl group, a $C_2$–$C_{40}$-alkenyl group, a $C_7$–$C_{40}$-arylalkyl group, a $C_7$–$C_{40}$-alkylaryl group or a $C_8$–$C_{40}$-arylalkenyl group, each of which can contain silicon, germanium, tin, oxygen, nitrogen, sulfur or phosphorus, e.g. a tri($C_1$–$C_{10}$-alkyl)silyl-$C_1$–$C_{20}$-alkyl group, or chelating ligands such as acetylacetonate or bipyridyl.

If Y is a $C_1$–$C_{40}$-group, this is covalently bonded to the metal atom M and together with the metal atom M can form a metallacycle, where, if Y is an unsaturated $C_1$–$C_{40}$-group, its π-electrons can coordinate to the metal atom M.

Examples of monodentate $C_1$–$C_{40}$-groups Y are $C_1$–$C_{20}$-alkyl, $C_2$–$C_{20}$-alkenyl or $C_6$–$C_{20}$-aryl. Examples of bidentate $C_1$–$C_{40}$-groups Y are $C_2$–$C_{40}$-alkenylene, acetylacetonate or bipyridyl.

The $C_1$–$C_{40}$-groups X can be saturated or unsaturated, linear, cyclic or branched and each be e.g. a $C_1$–$C_{20}$-alkylene group, a $C_6$–$C_{20}$-arylene group, a $C_2$–$C_{20}$-alkenylene group, a $C_7$–$C_{40}$-arylalkylene group, a $C_7$–$C_{40}$-alkylarylene group or a $C_8$–$C_{40}$-arylalkenylene group, each of which can contain silicon, germanium or tin, e.g. a tri($C_1$–$C_{10}$-alkyl)silyl-$C_1$–$C_{20}$-alkylene group. The group X is connecting L with the atom A and is preferably a bidentate group.

The $C_1$–$C_{40}$-groups $R^1$ can be saturated or unsaturated, linear, cyclic or branched and each be e.g. a $C_1$–$C_{20}$-alkyl group, a $C_1$–$C_{20}$-haloalkyl group, a $C_6$–$C_{20}$-aryl group, a $C_6$–$C_{20}$-haloaryl group, a $C_2$–$C_{20}$-alkenyl group, a $C_7$–$C_{40}$-arylalkyl group, a $C_7$–$C_{40}$-alkylaryl group or a $C_8$–$C_{40}$-arylalkenyl group. The groups $R^1$ are substituents of the atom A. Two or more groups $R^1$ can together form a ring system. The groups $R^1$ preferably contain halogen, in particular fluorine, e.g. $C_1$–$C_{20}$-haloalkyl or $C_6$–$C_{20}$-haloaryl, and can coordinate to the metal atom M via a halogen atom.

When M is a metal atom of group IV b of the Periodic Table of the Elements, it is preferred that n is 2, r is 1 or 2, and, if Y is an I-dentate $C_1$–$C_{40}$-group, I is 1 or 2.

Particular preference is given to compounds of the formula I in which

M is an element of group IVb of the Periodic Table of the Elements, for example titanium, zirconium or hafnium, n is 2, L are identical or different and are each a substituted or unsubstituted cyclopentadienyl group, where two radicals L can be connected to one another via a bridge Z, where Z is preferably $CR^2R^3$ or $SiR^2R^3$ or a unit Si—$(CR^2R^3)_x$—Si which links two groups $L_n(X_mA_tR^1_q)_sMY_r$ with one another, where $R^2$ and $R^3$ are identical or different and are each a $C_1$–$C_{20}$-hydrocarbon group such as $C_1$–$C_{10}$-alkyl or $C_6$–$C_{10}$-aryl, and x is an integer from 0 to 10, preferably x=6, Y are identical or different and are each a monodentate or bidentate, three-to to six-membered carbon-containing group which is saturated or unsaturated and can be substituted by $C_1$–$C_{40}$-groups such as $C_1$–$C_{10}$-alkyl, $C_6$–$C_{20}$-aryl or tri($C_1$–$C_{10}$-alkyl)silyl, r is 1 or 2, X is a $C_1$–$C_{20}$-hydrocarbon group, where m is 0 or 1, A is a metal atom of group IIIa, Va or VIa of the Periodic Table of the Elements, t is 1, $R^1$ are identical or different and are each a perhalogenated, preferably perfluorinated, $C_1$–$C_{20}$-group such as a perfluorinated $C_1$–$C_{10}$-alkyl group or a perfluorinated $C_6$–$C_{20}$-aryl group, q is 2, 3 or 4, and s is 1, 2, 3 or 4.

Y together with the metal atom M can here form a metallacycle and, if Y is an unsaturated three- to six-membered carbon-containing group, its π-electrons can coordinate to the metal atom M. A group $R^1$ can coordinate to the metal atom M via a halogen atom.

Very particular preference is given to compounds of the formula I in which

M is zirconium, n is 2,

L are identical or different and are each a substituted cyclopentadienyl group, where two radicals L are connected to one another via a bridge Z, where Z is preferably CR²R³ or SiR²R³, where R² and R³ are identical or different and are $C_1$–$C_{10}$-alkyl or $C_6$–$C_{10}$-aryl, Y is a monodentate unsaturated $C_5$-hydrocarbon group which can be substituted by $C_1$–$C_{10}$-alkyl groups, r is 1, m is 0, A is an atom of group IIIa of the Periodic Table of the Elements, e.g. a boron atom or an aluminum atom, t is 1, $R^1$ are identical and are each a pentafluorophenyl group ($C_6F_5$) and q is 3, and s is 1 or 2.

A pentafluorophenyl group can here coordinate to the metal atom M via a fluorine atom.

Examples of transition metal compounds of the invention having the formula I are:

[tris(pentafluorophenyl)(cyclopentadienylidene)borato](cyclopentadienyl)-1,2,3-trimethylpenta-1,3-dienylzirconium, [tris(pentafluorophenyl)(methylcyclopentadienylidene)borato](methylcyclopentadienyl)-1,2,3-trimethylpenta-1,3-dienylzirconium, [tris(pentafluorophenyl)(n-butylcyclopentadienylidene)borato](n-butylcyclopentadienyl)-1,2,3-trimethylpenta-1,3-dienylzirconium [tris(pentafluorophenyl)(indenylidene)borato](indenyl)-1,2,3-trimethylpenta-1,3-dienylzirconium, [tris(pentafluorophenyl)(cyclopentadienylidene)borato](tert-butylamido)dimethylsilane-1,2,3-trimethylpenta-1,3-dienylzirconium [tris(pentafluorophenyl)(2-methylbenzindenylidene)borato](2-methylbenzindenyl)1,2,3-trimethylpenta-1,3-dienylzirconium dimethylsilanediyl-[tris(pentafluorophenyl)(2-methylindenylidene)borato](2-methylindenyl)-1,2,3-trimethylpenta-1,3-dienylzirconium, dimethylsilanediyl-[tris(pentafluorophenyl)(indenylidene)borato](indenyl)-1,2,3-trimethylpenta-1,3-dienylzirconium, dimethylsilanediyl-[tris(pentafluorophenyl)(2-methylbenzindenylidene)borato](2-methylbenzindenyl)-1,2,3-trimethylpenta-1,3-dienylzirconium, dimethylsilanediyl-[tris(pentafluorophenyl)(2-methylindenylidene)borato](2-methylbenzindenyl)-1,2,3-trimethylpenta-1,3-dienyizirconium, dimethylsilanediyl-[tris(pentafluorophenyl)(2-methylbenzindenylidene)borato](2-methyl-4-phenylindenyl)-1,2,3-trimethylpenta-1,3-dienylzirconium, dimethylsilanediyl-[tris(pentafluorophenyl)(2-methylindenylidene)borato](4-phenylindenyl)-1,2,3-trimethylpenta-1,3-dienylzirconium, dimethylsilanediyl-[tris(pentafluorophenyl)(2-methyl-4-phenylindenylidene)borato](2-methyl-4-phenylindenyl)-1,2,3-trimethylpenta-1,3-dienylzirconium, dimethylsilanediyl-[tris(pentafluorophenyl)(2-methyl-4,6-diisopropylindenylidene)borato](2-methyl-4,6-diisopropylindenyl)-1,2,3-trimethylpenta-1,3-dienylzirconium, dimethylsilanediyl-[tris(pentafluorophenyl)(2-methyl-4-naphthylindenylidene)borato](2-methyl-4-naphthylindenyl)-1,2,3-trimethylpenta-1,3-dienylzirconium, isopropylidene-[tris(pentafluorophenyl)(cyclopentadienylidene)borato](fluorenyl)-1,2,3-trimethylpenta-1,3-dienylzirconium, isopropylidene-[tris(pentafluorophenyl)(cyclopentadienylidene)borato](indenyl)-1,2,3-trimethylpenta-1,3-dienylzirconium, [tris(pentafluorophenyl)(cyclopentadienylidene)borato](-4,7,7-trimethyl-(4,5,6,7-tetrahydroindenyl)-1,2,3-trimethylpenta-1,3-dienylzirconium, [tris(trifluoromethyl)(cyclopentadienylidene)borato](cyclopentadienyl)-1,2,3-trimethylpenta-1,3-dienylzirconium, [tris(trifluoromethyl)(methylcyclopentadienylidene)borato](methylcyclopentadienyl)-1,2,3-trimethylpenta-1,3-dienylzirconium, [tris(trifluoromethyl)(n-butylcyclopentadienylidene)borato](n-butylcyclopentadienyl)-1,2,3-trimethylpenta-1,3-dienylzirconium, [tris(trifluoromethyl)(indenylidene)borato](indenyl)-1,2,3-trimethylpenta-1,3-dienylzirconium, [tris(trifluoromethyl)(cyclopentadienylidene)borato](tert-butylamido)dimethylsilane-1,2,3-trimethylpenta-1,3-dienylzirconium, [tris(trifluoromethyl)(2-methylbenzindenylidene)borato](2-methylbenzindenyl)-1,2,3-trimethylpenta-1,3-dienylzirconium, dimethylsilanediyl-[tris(trifluoromethyl)(2-methylindenylidene)borato](2-methylindenyl)-1,2,3-trimethylpenta-1,3-dienylzirconium, dimethylsilanediyl-[tris(trifluoromethyl)(indenylidene)borato](indenyl)-1,2,3-trimethylpenta-1,3-dienylzirconium, dimethylsilanediyl-[tris(trifluoromethyl)(2-methylbenzindenylidene)borato](2-methylbenzindenyl)-1,2,3-trimethylpenta-1,3-dienylzirconium, dimethylsilanediyl-[tris(trifluoromethyl)(2-methylindenylidene)borato](2-methylbenzindenyl)-1,2,3-trimethylpenta-1,3-dienylzirconium, dimethylsilanediyl-[tris(trifluoromethyl)(2-methylbenzindenylidene)borato](2-methyl-4-phenylindenyl)-1,2,3-trimethylpenta-1,3-dienylzirconium, dimethylsilanediyl-[tris(trifluoromethyl)(2-methylindenylidene)borato](4-phenylindenyl)-1,2,3-trimethylpenta-1,3-dienylzirconium, dimethylsilanediyl-[tris(trifluoromethyl)(2-methyl-4-phenylindenylidene)borato](2-methyl-4-phenylindenyl)-1,2,3-trimethylpenta-1,3-dienylzirconium, dimethylsilanediyl-[tris(trifluoromethyl)(2-methyl-4,6-diisopropylindenylidene)borato](2-methyl-4,6-diisopropylindenyl)-1,2,3-trimethylpenta-1,3-dienylzirconium, dimethylsilanediyl-[tris(trifluoromethyl)(2-methyl-4-naphthylindenylidene)borato](2-methyl-4-naphthylindenyl)-1,2,3-trimethylpenta-1,3-dienylzirconium, isopropylidene-[tris(trifluoromethyl)(cyclopentadienylidene)borato](fluorenyl)-1,2,3-trimethylpenta-1,3-dienylzirconium, isopropylidene-[tris(trifluoromethyl)(cyclopentadienylidene)borato](indenyl)-1,2,3-trimethylpenta-1,3-dienylzirconium, [tris(trifluoromethyl)(cyclopentadienylidene)borato](-4,7,7-trimethyl-(4,5,6,7,-tetrahydroindenyl)-1,2,3-trimethylpenta-1,3-dienylzirconium, methylphenylmethylene-[tris(pentafluorophenyl)(cyclopentadienylidene)borato](fluorenyl)-1,2,3-trimethylpenta-1,3-dienylzirconium, diphenylmethylene-[tris(pentafluorophenyl)(cyclopentadienylidene)borato](fluorenyl)-1,2,3-trimethylpenta-1,3-dienylzirconium, isopropylidene-[tris(pentafluorophenyl)(-3-methylcyclopentadienylidene)borato](fluorenyl)-1,2,3-trimethylpenta-1,3-dienylzirconium, dimethylsilanediyl-[tris(pentafluorophenyl)(-3-(tert-butylcyclopentadienylidene)borato]-(fluorenyl)-1,2,3-trimethylpenta-1,3-dienylzirconium, diphenylsilanediyl-[tris(pentafluorophenyl)(-3-(trimethylsilyl)cyclopentadienylidene)borato]-(fluorenyl)-1, 2,3-trimethylpenta-1,3-dienylzirconium, methylphenylsilanediyl-[tris(pentafluorophenyl)(2-methylindenylidene)borate](2-methylindenyl)1,2,3-trimethylpenta-1,3-dienylzirconium, methylphenylsilanediyl-[tris(pentafluorophenyl)(indenylidene)borato](indenyl)-1,2,3-trimethylpenta-1,3-dienylzirconium, methylphenylisilanediyl-[tris(pentafluorophenyl)(2-methyl-4,5-benzindenylidene)borato](2-methyl-4,5-benzindenyl)-1,2,3-trimethylpenta-1,3-dienylzirconium methylphenylsilanediyl-[tris(pentafluorophenyl)(2-methylindenylidene)borato](2-methyl-4,5-benzindenyl)-1,2,3-trimethylpenta-1,3-dienylzirconium methylphenylsilanediyl-[tris(pentafluorophenyl)(2-methyl-4,5-benzindenylidene)borato](2-methyl-4-phenylindenyl)-1,2,3-trimethylpenta-1,3-dienylzirconium methylphenylsilanediyl-[tris(pentafluorophenyl)(2-methylindenylidene)borato](4-phenylindenyl)-1,2,3-trimethylpenta-1,3-dienylzirconium, methylphenylsilanediyl-[tris(pentafluorophenyl)(2-methyl-4-phenylindenylidene)borato](2-methyl-4-phenylindenyl)-1,2,3-trimethylpenta-1,3-dienylzirconium, methylphenylsilanediyl-[tris(pentafluorophenyl)(2-ethyl-4-phenylindenylidene)borato](2-ethyl-4-phenylindenyl)-1,2,3-trimethylpenta-1,3-dienylzirconium, methylphenylsilanediyl-[tris(pentafluorophenyl)(2-methyl-4,6-diisopropylindenylidene)-borato](2-methyl-4,6-diisoproylindenyl)-1,2,3-trimethylpenta-1,3-dienylzirconium, methylphenylsilanediyl-[tris(pentafluorophenyl)(2-methyl-4-naphthylindenylidene)-borato](2-methyl-4-naphthylindenyl)-1,2,3-trimethylpenta-1,3-dienylzirconium, ethylene-[tris(pentafluorophenyl)(indenylidene)borato](indenyl)-1,2,3-trimethylpenta-1,3-dienylzirconium, ethylene-[tris(pentafluorophenyl)(2-methylindenylidene)borato](2-methylindenyl)-1,2,3-trimethylpenta-1,3-dienylzirconium, ethylene-[tris(pentafluorophenyl)(2-methyl-4,5-benzindenylidene)borato](2-methyl-4,5-benzindenyl)-1,2,3-trimethylpenta-1,3-dienylzirconium, ethylene-[tris(pentafluorophenyl)(2-methylindenylidene)borato](2-methyl-4,5-benzindenyl)-1,2,3-trimethylpenta-1,3-dienylzirconium, ethylene-[tris(pentafluorophenyl)(2-methyl-4,5-benzindenylidene)borato](2-methyl-4-phenylindenyl)-1,2,3-dienylzirconium, ethylene-[tris(pentafluorophenyl)(2-methylindenylidene)borato](4-phenylindenyl)-1,2,3-trimethylpenta-1,3-dienylzirconium, ethylene-[tris(pentafluorophenyl)(2-methyl-4-phenylindenylidene)borato](2-methyl-4-phenylindenyl)-1,2,3-trimethylpenta-1,3-dienylzirconium, ethylene-[tris(pentafluorophenyl)(2-methyl-4,6-diisopropylindenylidene)borato](2-methyl-4,6-diisopropylindenyl)-1,2,3-trimethylpenta-1,3-dienylzirconium, ethylene-[tris(pentafluorophenyl)(2-methyl-4naphthylindenylidene)borato](2-methyl-4-naphthylindenyl)-1,2,3-trimethylpenta-1,3-dienylzirconium, ethylene-[tris(pentafluorophenyl)(2-ethyl-4-phenylindenylidene)borato](2-ethyl-4-phenylindenyl)-1,2,3-trimethylpenta-1,3-dienylzirconium, [bis(pentafluorophenyl)(cyclopentadienylidene)borane](cyclopentadienyl)-1,2,3-trimethylpenta-1,3-dienylzirconium, [bis(pentafluorophenyl)(methylcyclopentadienylidene)borane](methylcyclopentadienyl)-1,2,3-trimethylpenta-1,3-dienylzirconium, [bis(pentafluorophenyl)(n-butylcyclopentadienylidene)borane](n-butylcyclopentadienyl)-1,2,3-trimethylpenta-1,3-dienylzirconium, [bis(pentafluorophenyl)(indenylidene)borane](indenyl)-1,2,3-trimethylpenta-1,3-dienylzirconium, [bis(pentafluorophenyl)(cyclopentadienylidene)borane](tert-butylamido)dimethylsilane-1,2,3-trimethylpenta-1,3-dienylzirconium [bis(pentafluorophenyl)(2-methylbenzindenylidene)borane](2-methylbenzindenyl)-1,2,3-trimethylpenta-1,3-dienylzirconium, dimethylsilanediyl-[bis(pentafluorophenyl)(2-methylindenylidene)borane](2-methylindenyl)-1,2,3-trimethylpenta-1,3-dienylzirconium, dimethylsilanediyl-[bis(pentafluorophenyl)(indenylidene)borane](indenyl)-1,2,3-trimethylpenta-1,3-dienylzirconium, dimethylsilanediyl-[bis(pentafluorophenyl)(2-methylbenzindenylidene)borane](2-methylbenzindenyl)-1,2,3-trimethylpenta-1,3-dienylzirconium, dimethylsilanediyl-[bis(pentafluorophenyl)(2-methylindenylidene)borane](2-methylbenzindenyl)-1,2,3-trimethylpenta-1,3-dienylzirconium, dimethylsilanediyl-[bis(pentafluorophenyl)(2-methylbenzindenylidene)borane](2-methyl-4-phenylindenyl)-1,2,3-trimethylpenta-1,3-dienylzirconium, dimethylsilanediyl-]bis(pentafluorophenyl)(2-methylindenylidene)borane](4-phenylindenyl)-1,2,3-trimethylpenta-1,3-dienylzirconium, dimethylsilanediyl-[bis(pentafluorophenyl)(2-methyl-4-phenylindenylidene)borane](2-methyl-4-phenylindenyl)-1,2,3-trimethylpenta-1,3-dienylzirconium, dimethylsilanediyl-[bis(pentafluorophenyl)(2-methyl-4,6-diisopropylindenylidene)borane](2-methyl-4,6-diisopropylindenyl)-1,2,3-trimethylpenta-1,3-dienylzirconium, dimethylsilanediyl-[bis(pentafluorophenyl)(2-methyl-4-naphthylindenylidene)borane](2-methyl-4-naphthylindenyl)-1,2,3-trimethylpenta-1,3-dienylzirconium isopropylidene-[bis(pentafluorophenyl)(cyclopentadienylidene)borane](fluorenyl)-1,2,3-trimethylpenta-1,3-dienylzirconium, isopropylidene-[bis(pentafluorophenyl)(cyclopentadienylidene)borane](indenyl)-1,2,3-trimethylpenta-1,3-dienylzirconium, [bis(pentafluorophenyl)(cyclopentadienylidene)borane](4,7,7-trimethyl-(4,5,6,7,-tetrahydroindenyl)-1,2,3-trimethylpenta-1,3-dienylzirconium, [bis(trifluoromethyl)(cyclopentadienylidene)borane](cyclopentadienyl)-1,2,3-trimethylpenta-1,3-dienylzirconium, [bis(trifluoromethyl)(methylcyclopentadienylidene)borane](methylcyclopentadienyl)-1,2,3-trimethylpenta-1,3-dienylzirconium, [bis(trifluoromethyl)(n-butylcyclopentadienylidene)borane](n-butylcyclopentadienyl)-1,2,3-trimethylpenta-1,3-dienylzirconium, [bis(trifluoromethyl)(indenylidene)borane](indenyl)-1,2,3-trimethylpenta-1,3-dienylzirconium, [bis(trifluoromethyl)(cyclopentadienylidene)borane](tert-butylamido)dimethylsilane-1,2,3-trimethylpenta-1,3-dienylzirconium, [bis(trifluoromethyl)(2-methylbenzindenylidene)borane](2-methylbenzindenyl)-1,2,3-trimethylpenta-1,3-dienylzirconium, dimethylsilanediyl-[bis(trifluoromethyl)(2-methylindenylidene)borane](2-methylindenyl)-1,2,3-trimethylpenta-1,3-dienylzirconium, dimethylsilanediyl-[bis(trifluoromethyl)(indenylidene)borane](indenyl)-1,2,3-trimethylpenta-1,3-dienylzirconium, dimethylsilanediyl-[bis(trifluoromethyl)(2-methylbenzindenylidene)borane](2-methylbenzindenyl)-1,2,3-trimethylpenta-1,3-dienylzirconium, dimethylsilanediyl-[bis(trifluoromethyl)(2- methylindenylidene)borane](2-methylbenzindenyl)-1,2,3-trimethylpenta-1,3-dienylzirconium, dimethylsilanediyl-[bis(trifluoromethyl)(2-methylbenzindenylidene)borane](2-methyl-4-phenylindenyl)-1,2,3-trimethylpenta-1,3-dienylzirconium, dimethylsilanediyl-[bis(trifluoromethyl)(2-methylindenylidene)borane](4-phenylindenyl)-1,2,3-trimethylpenta-1,3-dienylzirconium, dimethylsilanediyl-]bis(trifluoromethyl)(2-methyl-4-phenylindenylidene)borane](2-methyl-4-phenylindenyl)-1,2,3-trimethylphenta-1,3-dienylzirconium, dimethylsilanediyl-[bis(trifluoromethyl)(2-methyl-4,6-diisopropylindenylidene)borane](2-methyl-4,6-diisopropylindenyl)-1,2,3-trimethylpenta-1,3-dienylzirconium, dimethylsilanediyl-[bis(trifluoromethyl)(2-methyl-4-naphthylindenylidene)borane](2-methyl-4-naphthylindenyl)-1,2,3-trimethylpenta-1,3-dienylzirconium, isopropylidene-[bis(trifluoromethyl)(cyclopentadienylidene)borane](fluorenyl)-1,2,3-trimethylpenta-1,3-dienylzirconium, isopropylidene-[bis(trifluoromethyl)(cyclopentadienylidene)borane](indenyl)-1,2,3-trimethylpenta-1,3-dienylzirconium, [bis(trifluoromethyl)(cyclopentadienylidene)borane](4,7,7-trimethyl-(4,5,6,7,-tetrahydroindenyl)-1,2,3-trimethylpenta-1,3-dienylzirconium, methylphenylmethylene-[bis(pentafluorophenyl)(cyclopentadienylidene)borane](fluorenyl)-1,2,3-trimethylpenta-1,3-dienylzirconium, diphenylmethylene-[bis(pentafluorophenyl)(cyclopentadienylidene)borane](fluorenyl)-1,2,3-trimethylpenta-1,3-dienylzirconium, isopropylidene-[bis(pentafluorophenyl)(3-methylcyclopentadienylidene)borane](fluorenyl)-1,2,3-trimethylpenta-1,3-dienylzirconium, dimethylsilanediyl-[bis(pentafluorophenyl)(3-(tert-butylcyclopentadienylidene)borane](fluorenyl)-1,2,3-trimethylpenta-1,3-dienylzirconium, diphenylsilanediyl-[bis(pentafluorophenyl)(3-(trimethylsilyl)cyclopentadienylidene)borane](fluorenyl)-1,2,3-trimethylpenta-1,3-dienylzirconium, methylphenylsilanediyl-[bis(pentafluorophenyl)(2-methylindenylidene)borane](2-methylindenyl)-1,2,3-trimethylpenta-1,3-dienylzirconium, methylphenylsilanediyl-[bis(pentafluorophenyl)(indenylidene)borane](indenyl)-1,2,3-trimethylpenta-1,3-dienylzirconium, methylphenylisilanediyl-[bis(pentafluorophenyl)(2-methyl-4,5-benzindenylidene)borane](2-methyl-4, 5-benzindenyl)-1,2,3-trimethylpenta-1,3-dienylzirconium methylphenylsilanediyl-[bis(pentafluorophenyl)(2-methylindenylidene)borane](2-methyl-4,5-benzindenyl)-1,2,3-trimethylpenta-1,3-dienylzirconium, methylphenylsilanediyl-[bis(pentafluorophenyl)(2-methyl-4,5-benzindenylidene)borane](2-methyl-4-phenylindenyl)-1,2,3-trimethylpenta-1,3-dienylzirconium, methylphenylsilanediyl-[bis(pentafluorophenyl)(2-methylindenylidene)borane](4-phenylindenyl)-1,2,3-trimethylpenta-1,3-dienylzirconium, methylphenylsilanediyl-[bis(pentafluorophenyl)(2-methyl-4-phenylindenylidene)borane](2-methyl-4-phenylindenyl)-1,2,3-trimethylpenta-1,3-dienylzirconium methylphenylsilanediyl-[bis(pentafluorophenyl)(2-ethyl-4-phenylindenylidene)borane](2-ethyl-4-phenylindenyl)-1,2,3-trimethylpenta-1,3-dienylzirconium methylphenylsilanediyl-[bis(pentafluorophenyl)(2-methyl-4,6-diisopropylindenylidene)borane](2-methyl-4,6-diisopropylindenyl)-1,2,3-trimethylpenta-1,3-dienylzirconium, methylphenylsilanediyl-[bis(pentafluorophenyl)(2-methyl-4-naphthyl-indenylidene)borane](2-methyl-4-naphthylindenyl)-1,2,3-trimethylpenta-1,3-dienylzirconium ethylene-[bis(pentafluorophenyl)(indenylidene)borane](indenyl)-1,2,3-trimethylpenta-1,3-dienylzirconium, ethylene-[bis(pentafluorophenyl)(2-methylindenylidene)borane](2-methylindenyl)-1,2,3-trimethylpenta-1,3-dienylzirconium, ethylene-[bis(pentafluorophenyl)(2-methyl-4,5-benzindenylidene)borane](2-methyl-4,5-benzindenyl)-1,2,3-trimethylpenta-1,3-dienylzorconium, ethylene-[bis(pentafluorophenyl)(2-methylindenylidene)borane](2-methyl-4,5-benzindenyl)-1,2,3-trimethylpenta-1,3-dienylzirconium, ethylene-[bis(pentafluorophenyl)(2-methyl-4,5-benzindenylidene)borane](2-methyl-4-phenylindenyl)-1,2,3-trimethylpenta-1,3-dienylzirconium, ethylene-[bis(pentafluorophenyl)(2-methylindenylidene)borane](4-phenylindenyl)-1,2,3-trimethylpenta-1,3-dienylzirconium, ethylene-[bis(pentafluorophenyl)(2-methyl-4-phenyl-indenylidene)borane](2-methyl-4-phenylindenyl)-1,2,3-trimethylpenta-1,3-dienylzirconium ethylene-[bis(pentafluorophenyl)(2-methyl-4,6-diisopropylindenylidene)borane](2-methyl-4,6-diisopropylindenyl)1,2,3-trimethylpenta-1,3-dienylzirconium, ethylene-[bis(pentafluorophenyl)(2-methyl-4-naphthyl-indenylidene)borane](2-methyl-4-naphthylindenyl)-1,2,3-trimethylpenta-1,3-dienylzirconium ethylene-[bis(pentafluorophenyl)(2-ethyl-4-phenyl-indenylidene)borane](2-ethyl-4-phenylindenyl)-1,2,3-trimethylpenta-1,3-dienylzirconium,

[tris(pentafluorophenyl)(cyclopentadienylidene)borato](cyclopentadienyl)-1,2,3,4-tetraphenylbuta-1,3-dienylzirconium, [tris(pentafluorophenyl)(2-methylbenzindenylidene)borato](2-methylbenzindenyl)-1,2,3,4-tetraphenylbuta-1,3-dienylziconium, dimethylsilanediyl-[tris(pentafluorophenyl)(2-methyl-indenylidene)borato](2-methyl-indenyl)-1,2,3,4-tetraphenylbuta-1,3-dientylzirconium, dimethylsilanediyl-[tris(pentafluorophenyl)(2-methylbenzindenylidene)borato](2-methyl-4-phenylindenyl)-1,2,3,4-tetraphenylbuta-1,3-dienylzirconium, dimethylsilanediyl-[tris(pentafluorophenyl)(2-methyl-4-phenylindenylidene)borato](2-methyl-4-phenylindenyl)-1,2,3,4-tetraphenylbuta-1,3-dienylzirconium, dimethylsilanedenyl-[tris(pentafluorophenyl)(2-methyl-4-naphthylindenylidene)borato](2-methyl-4-naphthylindenyl)-1,2,3,4-tetraphenylbuta-1,3-dienylzirconium isopropylidene-[tris(pentafluorophenyl)(cyclopentadienylidene)borato](fluorenyl)-1,2,3,4-tetraphenylbuta-1,3-dienylzirconium, dimethylsilanediyl-[tris(trifluoromethyl)(2-methylbenzindenylidene)borato](2-methylbenzindenyl-)-1,2,3,4-tetraphenylbuta-1,3-dienylzirconium, dimethylsilanediyl-[tris(trifluoromethyl)(2-methyl-4-phenylindenylidene)borato](2-methyl-4-phenylindenyl)-1,2,3,4-tetraphenylbuta-1,3-dienylzirconium, dimethylsilanediyl-[tris(trifluoromethyl)(2-methyl-4,6-diisopropylindenylidene)borato](2-methyl-4,6-diisopropylindenyl)-1,2,3,4-tetraphenylbuta-1,3-dienylzirconium, methylphenylmethylene-[tris(pentafluorophenyl)(cyclopentadienylidene)borato](fluorenyl)-1,2,3,4-tetraphenylbuta-1,3-dienylzirconium, methylphenylsilanediyl-[tris(pentafluorophenyl)(2-methyl-4,5-benzindenylidene)borato](2-methyl-4,5-benzindenyl)-1,2,3,4-tetraphenylbuta-1,3-dienylzirconium methylphenyisilanediyl-[tris(pentafluorophenyl)(2-ethyl-4-phenyl-indenylidene)borato](2-ethyl-4-phenylindenyl)-1,2,3,4-tetraphenylbuta-1,3-dienylzirconium ethylene-[tris(pentafluorophenyl)(2-methylindenylidene)borato](2-methylindenyl)-1,2,3,4-tetraphenylbuta-1,3-dienylzirconium, [tris(pentafluorophenyl)(cyclopentadienylidene)borato](cyclopentadienyl)-1-methyl-2,3-cyclohexylene-penta-1,3-dienylzirconium, dimethylsilanediyl-[tris(pentafluorophenyl)(2-methyl-4-phenylindenylidene)borato](2-methyl-4-phenylindenyl)1-methyl-2,3-cyclohexylene-penta-1,3-dienylzirconium, [tris(pentafluorophenyl)(cyclopentadienylidene)borato](cyclopentadienyl)-1,4-di(trimethylsilyl)-2,3-dimethylbuta-1,3-dienylzirconium, dimethylsilanediyl-[tris(pentafluorophenyl)(2-methyl-4-phenylindenylidene)borato](2-methyl-4-phenylindenyl)-1,4-di(trimethylsilyl)-2,3-dimethylbuta-1,3-dienylzirconium, [tris(pentafluorophenyl)(cyclopentadienylidene)borato](cyclopentadienyl)acetylacetonatozirconium, dimethylsilanediyl-[tris(pentafluorophenyl)(2-methyl-4-phenylindenylidene)borato](2-methyl-4-phenylindenyl)acetylacetonatozirconium, [tris(pentafluorophenyl)(cyclopentadienylidene)borato](cyclopentadienyl)bipyridylzirconium, dimethylsilanediyl-[tris(pentafluorophenyl)(2-methyl-4-phenylindenylidene)borato](2-methyl-4-phenylindenyl)bipyridylzirconium, [tris(pentafluorophenyl)(cyclopentadienylidene)borato](cyclopentadienyl)chlorozirconium, dimethylsilanediyl]tris(pentafluorophenyl)(2-methyl-4-phenylindenylidene)borato](2-methyl-4-phenylindenyl)chlorozirconium, [tris(pentafluorophenyl)(cyclopentadienylidene)borato]bis(cyclopentadienyl)zirconium, [tris(pentafluorophenyl)(2-methylbenzindenylidene)borato](2-methylbenzindenyl)methylzirconium, dimethylsilanediyl[tris(pentafluorophenyl)(2-methylindenylidene)borato](2-methylindenyi)methylzirconium, dimethylsilanediyl[tris pentafluorophenyl)(2-methylbenzindenylidene)borato](2-methyl-4-phenylindenyl)methylzirconium, dimethylsilanediyl[tris(pentafluorophenyl)(2-methyl-4-naphthylindenylidene)borato](2-methyl-4-naphthylindenyl)methylzirconium, isopropylidene-[tris(pentafluorophenyl)(cyclopentadienylidene)borato](fluorenyl)methylzirconium, dimethylsilanediyl[tris(trifluoromethyl)(2-methylbenzindenylidene)borato](2-methylbenzindenyl)methylzirconium, dimethylsilanediyl[tris(trifluoromethyl)(2-methyl-4-phenylindenylidene)borato](2-methyl-4-phenylindenyl)methylzirconium, dimethylsilanediyl[tris(trifluoromethyl)(2-methyl-4,6-diisopropylindenylidene)borato](2-methyl-4,6-diisopropylindenyl)methylzirconium, methylphenylmethylene[tris(pentafluorophenyl)(cyclopentadienylidene)borato](fluorenyl)methylzirconium, methylphenylsilanediyl[tris(pentafluorophenyl)(2-methyl-4,5-benzindenylidene)borato](2-methyl-4,5-benzindenyl)methylzirconium, methylphenylsilanediyl[tris(pentafluorophenyl)(2-ethyl-4-phenyl-indenylidene)borato](2-ethyl-4-phenylindenyl)methylzirconium, ethylene[tris(pentafluorophenyl)(2-methylindenylidene)borato](2-methylindenyl)methylzirconium, [tris(pentafluorophenyl)(2-methylbenzindenylidene)borato](2-methylbenzindenyl)phenylzirconium, dimethylsilanediyl[tris(pentafluorophenyl)(2-methylindenylidene)borato](2-methylindenyl)phenylzirconium, dimethylsilanediyl[tris(pentafluorophenyl)(2-methyl-4-naphthylindenylidene)borato](2-methyl-4-phenylindenyl)phenylzirconium, dimethylsilandenyl[tris(pentafluorophenyl)(2-methyl-4-naphthylindenylidene)borato](2-methyl-4-naphthylindenyl)phenylzirconium, isopropylidene[tris(pentafluorophenyl)(cyclopentadienylidene)borato](fluorenyl)phenylzircononium dimethylsilanediyl[tris(trifluoromethyl)(2-methylbenzindenylidene)borato](2-methylbenzindenyl)phenylzirconium dimethylsilanediyl[tris(trifluoromethyl)(2-methyl-4-phenylindenylidene)borato](2-methyl-4-phenylindenyl)phenylzirconium dimethylsilanediyl[tris(trifluoromethyl)(2-methyl-4,6-diisopropylindenylidene)borato](2-methyl-4,6-diisopropylindenyl)phenylzirconium methylphenylmethylene[tris(pentafluorophenyl)(cyclopentadienylidene)borato]fluorenyl)phenylzirconium methylphenylisilanediyl[tris(pentafluorophenyl)(2-methyl-4,5-benzindenylidene)borato](2-methyl-4,5-benzindenyl)phenylzirconium methylphenylsilanediyl[tris(pentafluorophenyl)(2-ethyl-4-phenyl-indenylidene)borato](2-ethyl-4-phenylindenyl)phenylzirconium ethylene[tris(pentafluorophenyl)(2-methylindenylidene)borato](2-methylindenyl)phenylzirconium [bis(pentafluorophenyl)(cyclopentadienylidene)borane](cyclopentadienyl)-1,2,3,4-tetraphenylbuta-1,3-dienylzirconium [bis(pentafluorophenyl)(2-methylbenzindenylidene)borane](2-methylbenzindenyl)-1,2,3,4-tetraphenylbuta-1,3-dienylzirconium dimethylsilanediyl[bis(pentafluorophenyl)(2-methyl-indenylidene)borane](2-methylindenyl)-1,2,3,4-tetraphenylbuta-1,3-dienylzirconium dimethylsilanediyl[bis(pentafluorophenyl)(2-methylbenzindenylidene)borane](2-methyl-4-phenylindenyl)-1,2,3,4-tetraphenylbuta-1,3-dienylzirconium dimethylsilanediyl[bis(pentafluorophenyl)(2-methyl-4-phenylindenylidene)borane](2-methyl-4-phenylindenyl)-1,2,3,4-tetraphenylbuta-1,3-dienylzirconium dimethylsilanediyl[bis(pentafluorophenyl)(2-methyl-4-naphthylindenylidene)borane](2-methyl-4-naphthylindenyl)-1,2,3,4-tetraphenylbuta-1,3-dienylzirconium isopropylidene[bis(pentafluorophenyl)(cyclopentadienylidene)borane](fluorenyl)-1,2,3,4-tetraphenylbuta-1,3-dienylzirconium dimethylsilanediyl[bis(trifluoromethyl)(2-methylbenzindenylidene)borane](2-methylbenzindenyl)-1,2,3,4-tetraphenylbuta-1,3-dienylzirconium, dimethylsilanediyl[bis(trifluoromethyl)(2-methyl-4-phenylindenylidene)borane](2-methyl-4-phenylindenyl)-1,2,3,4-tetraphenylbuta-1,3-dienylzirconium, dimethylsilanediyl[bis(trifluoromethyl)(2-methyl-4,6-diisopropylindenylidene)borane](2-methyl-4,6-diisopropylindenyl)-1,2,3,4-tetraphenylbuta-1,3-dienylzirconium, methylphenylmethylene[bis(pentafluorophenyl)(cyclopentadienylidene)borane](fluorenyl)-1,2,3,4-tetraphenylbuta-1,3-dienylzirconium- methylphenylsilanediyl[bis(pentafluorophenyl)(2-methyl-4,5-benzindenylidene)borane](2-methyl-4,5-benzindenyl)-1,2,3,4-tetraphenylbuta-1,3-dienylzirconium methylphenyisilanediyl[bis(pentafluorophenyl)(2-ethyl-4-phenyl-indenylidene)borane](2-ethyl-4-phenylindenyl)-1,2,3,4-tetraphenylbuta-1,3-dienylzirconium ethylene[bis(pentafluorophenyl)(2-methylindenylidene)borane](2-methylindenyl)-1,2,3,4-tetraphenylbuta-1,3-dienylzirconium, [bis(pentafluorophenyl)(cyclopentadienylidene)borane](cyclopentadienyl)-1- methyl-2,3-cyclohexylene-penta-1,3-dienylzirconium, dimethylsilanediyl[bis(pentafluorophenyl)(2-methyl-4-phenylindenylidene)borane](2-methyl-4-phenylindenyl)-1-methyl-2,3-cyclohexylene-penta-1,3-dienylzirconium[bis(pentafluorophenyl)(cyclopentadienylidene)borane](cyclopentadienyl)-1,4-di(tri-methylsilyl)-2,3-dimethylbuta-1,3-dienylzirconium dimethylsilanediyl[bis(pentafluorophenyl)(2-methyl-4-phenylindenylidene)borane](2-methyl-4-phenylindenyl)-1,4-di(trimethylsilyl)-2,3-dimethylbuta-1,3-dienylzirconium, [bis(pentafluorophenyl)(cyclopentadienylidene)borane](cyclopentadienyl)acetylacetonatozirconium, dimethylsilanediyl[bis(pentafluorophenyl)(2-methyl-4-phenylindenylidene)borane](2-methyl-4-phenylindenyl)acetylacetonatozirconium, [bis(pentafluorophenyl)(cyclopentadienylidene)borane](cyclopentadienyl)bipyridylzirconium, dimethylsilanediyl[bis(pentafluorophenyl)(2-methyl-4-phenylindenylidene)borane](2-methyl-4-phenylindenyl)bipyridylzirconium, [bis(pentafluorophenyl)(cyclopentadienylidene)borane](cyclopentadienyl)dichlorozirconium dimethylsilanediyl[bis(pentafluorophenyl)(2-methyl-4-phenylindenylidene)borane](2-methyl-4-phenylindenyl)dichlorozirconium, [bis(pentafluorophenyl)(2-methylbenzindenylidene)borane](2-methylbenzindenyl)dimethylzirconium, dimethylsilanediyl[bis(pentafluorophenyl)(2-methylindenylidene)borane](2-methylindenyl)dimethylzirconium, dimethylsilanediyl[bis(pentafluorophenyl)(2-methylbenzindenylidene)borane](2-methyl-4-phenylindenyl)dimethylzirconium, dimethylsilanediyl[bis(pentafluorophenyl)(2-methyl-4-naphthylindenylidene)borane](2-methyl-4-naphthylindenyl)dimethylzirconium, Isopropylidene[bis(pentafluorophenyl)(cyclopentadienylidene)borane](fluorenyl)dimethylzirconium, dimethylsilanediyl[bis(trifluoromethyl)(2-methylbenzindenylidene)borane](2-methylbenzindenyl)dimethylzirconium, dimethylsilanediyl[bis(trifluoromethyl)(2-methyl-4-phenylindenylidene)borane](2-methyl-4-phenylindenyl)dimethylzirconium, dimethylsilanediyl[bis(trifluoromethyl)(2-methyl-4,6-diisopropylindenylidene)borane](2-methyl-4,6-diisopropylindenyl)dimethylzirconium, methylphenylmethylene[bis(pentafluorophenyl)(cyclopentadienylidene)borane](fluorenyl)dimethylzirconium, methylphenylsilanediyl[bis(pentafluorophenyl)(2-methyl-4,5-benzindenylidene)borane](2-methyl-4,5-benzindenyl)dimethylzirconium, methylphenylsilanediyl[bis(pentafluorophenyl)(2-ethyl-4-phenyl-indenylidene)borane](2-ethyl-4-phenylindenyl)dimethylzirconium, ethylene[bis(pentafluorophenyl)(2-methylindenylidene)borane](2-methylindenyl)dimethylzirconium, [bis(pentafluorophenyl)(2-methylbenzindenylidene)borane](2-methylbenzindenyl)diphenylzirconium, dimethylsilanediyl[bis(pentafluorophenyl)(2-methylindenylidene)borane](2-methylindenyl)diphenylzirconium, dimethylsilanediyl[bis(pentafluorophenyl)(2-methylbenzindenylidene)borane](2-methyl-4-phenylindenyl)dipeneylzirconium, dimethylsilanediyl[bis(pentafluorophenyl)(2-methyl-4-naphthylindenylidene)borane](2-methyl-4-naphthylindenyl)diphenylzirconium, isopropylidene[bis(pentafluorophenyl)(cyclopentadienylidene)borane](fluorenyl)diphenylzirconium, dimethylsilanediyl[bis(trifluoromethyl)(2-methylbenzindenylidene)borane](2-methylbenzindenyl)diphenylzirconium, dimethylsilanediyl[bis(trifluoromethyl)(2-methyl-4-phenylindenylidene)borane](2-methyl-4-phenylindenyl)diphenylzirconium, dimethylsilanediyl[bis(trifluoromethyl)(2-methyl-4,6-diisopropylindenylidene)borane](2-methyl-4,6-diisopropylindenyl)diphenylzirconium, methylphenylmethylene[bis(pentafluorophenyl)(cyclopentadienylidene)borane](fluorenyl)diphenylzirconium, methylphenylsilanediyl[bis(pentafluorophenyl)(2-methyl-4,5-benzindenylidene)borane](2-methyl-4,5-benzindenyl)diphenylzirconium, methylphenylsilanediyl[bis(pentafluorophenyl)(2-ethyl-4-phenyl-indenylidene)boraneI(2-ethyl-4-phenylindenyl)diphenylzirconium and ethylene[bis(pentafluorophenyl)(2-methylindenylidene)borane](2-methylindenyl)diphenylzirconium.

The preparation of the transition metal compounds of the invention having the formula I is illustrated by the following reaction scheme.

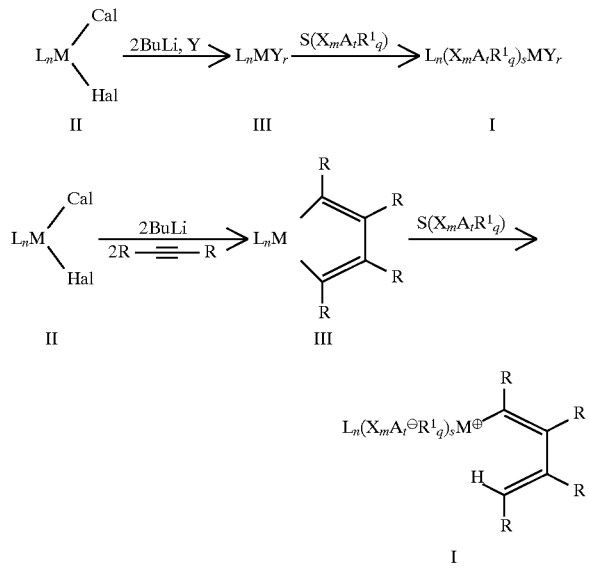

In this scheme, L, n, M, Y, r, s, t, A, $R^1$, X, m and q are as defined above for formula I, R is a $C_1$–$C_{40}$-group such as $C_1$–$C_{10}$-alkyl, $C_6$–$C_{20}$-aryl or tri($C_1$–$C_{10}$alkyl)silyl and Hal is a halogen such as fluorine or chlorine. Compounds of the formula II are widely described in the literature (J. Okuda, Topics in Current Chemistry, Vol. 160; Springer Verlag, Berlin Heidelberg 1991, page 97).

The reaction of compounds of the formula II in inert solvents with alkyllithium compounds (such as butyllithium (BuLi)) and alkyne compounds (such as 2-butyne, 3-hexyne, diphenylacetylene, trimethylsilylphenylacetylene (1-trimethylsilyl-2-phenylethyne)) can lead, with elimination of a salt, to formation of cyclic systems (metallocyclopentadienes) of the formula III in which the M—Y bond is covalent.

The reaction of the compounds of the formula IIII with Lewis acids of the formula $X_mA_rR^1_q$ is carried out in organic solvents such as toluene, benzene, methylene chloride, carbon tetrachloride and petroleum spirit. This gives a transition metal compound of the formula I in which the M—Y bond is covalent. Transition metal compounds of the formula I in which Y is an unsaturated hydrocarbon group such as a diene unit can be reacted with chelating reagents such as acetylacetone to give transition metal compounds of the formula I in which Y is a chelate ligand such as acetylacetonate.

The transition metal compound of the invention having the formula I can be isolated or used directly for further reactions. The transition metal compounds of the formula I can also be prepared without isolation of intermediates and final products in a single-vessel reaction from transition metal dihalides, dianion compounds and Lewis acids and used directly for the polymerization.

Suitable solvents are aliphatic or aromatic solvents such as hexane or toluene or halogenated hydrocarbons such as methylene chloride or halogenated aromatic hydrocarbons such as o-dichlorobenzene.

A further possible way of preparing the transition metal compounds of the invention comprises the formation of metallacycles of the formula III by reaction of $L_nMR^4_2$ ($R^4$ are identical or different and are CO, H, $CH_3$) with the corresponding alkyne followed by reaction with the appropriate Lewis acid.

The reaction of sodium cyclopentadienide with $X_mA_rR^1_q$ in inert solvents and further reaction with $MCl_4$ likewise leads to the compound I of the invention.

The present invention also provides a process for preparing a polyolefin by polymerization of one or more olefins in the presence of a catalyst comprising at least one transition metal compound of the formula I. The term polymerization includes both homopolymerization and copolymerization.

Preference is given to polymerizing olefins of the formula $R^a$—CH=CH—$R^b$, where $R^a$ and $R^b$ are identical or different and are each a hydrogen atom or a carbon-containing radical having from 1 to 20 carbon atoms, in particular from 1 to 10 carbon atoms, and $R^a$ and $R^b$ together with the atoms connecting them can form one or more rings. Examples of such olefins are 1-olefins having from 2 to 40, preferably from 2 to 10 carbon atoms, for example ethylene, propylene, 1-butene, 1-pentene, 1-hexene, 4-methyl-1-pentene or 1-octene, styrene, dienes such as 1,3-butadiene, 1,4-hexadiene, vinylnorbornene or norbornadiene and cyclic olefins such as norbornene, tetracyclododecene or methyinorbornene. In the process of the invention, preference is given to homopolymerizing ethylene or propylene, or copolymerizing ethylene with one or more 1-olefins having from 3 to 20 carbon atoms, for example propylene, and/or one or more dienes having from 4 to 20 carbon atoms, for example, 1,4-butadiene or norbornadiene. Examples of such copolymers are ethylene-propylene copolymers and ethylene-propylene-1,4-hexadiene copolymers.

The polymerization is preferably carried out at a temperature of from −60° to 250° C., particularly preferably from 50° to 200° C. The pressure is preferably from 0.5 bis 2000 bar, particularly preferably from 5 to 64 bar.

The polymerization can be carried out in solution, in bulk, in suspension or in the gas phase, continuously or batchwise, in one or more stages.

The catalyst used in the process of the invention preferably comprises one transition metal compound of the formula I. It is also possible to use mixtures of two or more transition metal compounds of the formula I or mixtures of transition metal compounds of the formula I with metallocenes or classical Ziegler-Natta catalysts, for example for preparing polyolefins having a broad or multimodal molecular weight distribution.

A prepolymerization can be carried out with the aid of the transition metal compound of the invention having the formula I. For the prepolymerization, preference is given to using the (or one of the) olefin(s) used in the polymerization.

The transition metal compounds of the formula I can also be applied to a support. Application to a support allows, for example, the particle morphology of the polyolefin prepared to be controlled. Suitable support materials are, for example, silica gels, aluminum oxides, solid aluminoxane or other inorganic support materials such as magnesium chloride. Another suitable support material is a polyolefin powder in finely divided form.

The supported catalyst system can be resuspended as powder or while still containing solvent and be metered as suspension in an inert suspension medium into the polymerization system.

Before addition of the catalyst, in particular the supported catalyst system (comprising a transition metal compound of the formula I and a support material), it is advantageous to carry out a purification using an aluminum alkyl compound such as trimethylaluminum, triethylaluminum, triisobutylaluminum, trioctylaluminum or isoprenylaluminum for making the polymerization system inert (for example for removing catalyst poisons present in the olefin). This purification can be carried out either in the polymerization system itself or the olefin is, prior to addition to the polymerization system, brought into contact with the Al compound and subsequently separated off again. If this purification is carried out in the polymerization system itself, the aluminum alkyl compound is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents.

In principle, the use of further substances for catalyzing the polymerization reaction is not necessary, i.e. the transition metal compounds of the invention having the formula I can be used without a cocatalyst for olefin polymerization. As molecular weight regulator and/or for increasing the activity, hydrogen is added if necessary. The total pressure in the polymerization system is from 0.5 to 2500 bar, preferably from 2 to 1500 bar.

The catalyst system is here used in a concentration, based on the transition metal, of preferably from $10^{-3}$ to $10^{-8}$ mol, preferably from $10^{-4}$ to $10^{-7}$ mol, of transition metal per $dm^3$ of solvent or per $dm^3$ of reactor volume.

If the polymerization is carried out as a suspension or solution polymerization, an inert solvent customary for the Ziegler low-pressure process is used. For example, it is carried out in an aliphatic or cycloaliphatic hydrocarbon, examples of which are propane, butane, hexane, heptane, isooctane, cyclohexane and methylcyclohexane. It is also possible to use a petroleum or hydrogenated diesel oil fraction. Toluene can also be used. Preference is given to carrying out the polymerization in the liquid monomer.

If inert solvents are used, the monomers are metered in in gaseous or liquid form.

The polymerization time can be any desired, since the catalyst system to be used according to the invention displays only a small time-dependent drop in the polymerization activity.

The polymers prepared by the process of the invention are particularly suitable for producing shaped bodies such as films, sheets or large hollow bodies (e.g. tubes).

The following examples serve to illustrate the invention.

General procedures: preparation and handling of organometallic compounds were carried out with exclusion of air and moisture under argon protection (Schlenk technique). All solvents required were made absolute prior to use by boiling for a number of hours over a suitable desiccant and subsequent distillation under argon.

The compounds were characterized by $^1$H-HMR, $^{13}$C-NMR and IR-spectroscopy.

EXAMPLE 1

[Tris(pentafluorophenyl)(η⁵-cyclopentadienylidene)borato](η⁵-cyclopentadienyl)(1,2,3-trimethylpenta-1,3-dienyl)zirconium

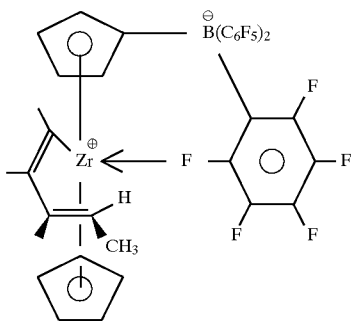

a) 1-bis(η⁵-cyclopentadiene)zircona-2,3,4,5-tetramethylcyclopentadiene 4.5 ml (7.1 mmol) of a 1.6M solution of n-butyllithium in hexane is added dropwise to a solution of 1 g (3.40 mmol) of zirconocene dichloride in 20 ml of THF cooled to −78° C. The mixture is left stirring for 24 hours and, at −78° C., a solution of 0.55 g (0.8 ml, 10.2 mmol) of 2-butyne in 10 ml of THF is allowed to run in dropwise. The mixture is very slowly allowed to warm to room temperature and the solvent is then removed in an oil pump vacuum. The solid residue is extracted twice with 30 ml of pentane and the combined pentane phases are evaporated to dryness in an oil pump vacuum. This gives 1.09 g (98%) of a red-brown powder.

b) [Tris(pentafluorophenyl)(η⁵-cyclopentadienylidene)borato](η⁵-cyclopentadienyl)( 1,2,3-trimethylpenta-1,3-dienyl)zirconium 2 mmol of bis(η⁵-cyclopentadienyl)zircona-2,3,4,5-tetramethylcyclopentadiene are dissolved in 50 ml of toluene and admixed with a solution of 2 mmol of tris(pentafluorophenyl)borane in 35 ml of toluene. The brown solution obtained is stirred for eight hours at room temperature and is then freed of the solvent. The remaining brown residue is washed twice with 25 ml of pentane and then dried in an oil pump vacuum. This gives 1.12 g of a yellow powder which is readily soluble in toluene, methylene chloride and THF.

EXAMPLE 2

Dimethylsilanediyl[tris(pentafluorophenyl)(2-methyl-4,5-benzoindenylidene)borato](2-methyl-4,5-benzoindenyl)-1,2,3-trimethylpenta-1,3-dienylzirconium 4 ml of a 1.6M solution of butyllithium in hexane is added dropwise to a solution of 3 mmol of dimethylsilanediyl(2-methyl-4,5-benzoindenyl)zirconium dichloride in 20 ml of THF cooled to −78° C. The mixture is stirred for a further 24 hours and a solution of 9 mmol of 2-butyne in 10 ml of THF is added dropwise at −78° C. The mixture is temperature and the solvent is removed in an oil pump vacuum. The solid residue is extracted twice with 30 ml of pentane and the combined pentane phases are evaporated to dryness in an oil pump vacuum. This gives dimethylsilanediylbis(2-methyl-4,5-benzoindenyl)zircona-2,3,4,5-tetramethylcyclopentadiene as a pulverulent solid in a yield 96%.

2 mmol of this metallacycle are dissolved in 50 ml of toluene and admixed with a solution of 2 mmol of tris(pentafluorophenyl)borane in 35 ml of toluene. The brown solution obtained is stirred for eight hours at room temperature and is then freed of the solvent. The remaining brown residue is washed with pentane and dried in an oil pump vacuum. This gives dimethylsilanediyl[tri(pentafluorophenyl(2-methyl-4,5-benzoindenylidene)borato](2-methyl-4, 5-benzoindenyl-1,2,3-trimethylpenta-1,3-dienylzirconium in a yield of 76%.

EXAMPLE 3

[Tris(pentafluorophenyl)(η⁵-cyclopentadienylidene)borato](η⁵-cyclopentadienyl)acetylacetonatozirconium 2 mmol of [tris(pentafluorophenyl)(η⁵-cyclopentadienylidene)borato](η⁵-cyclopentadienyl)(1,2,3-trimethylpenta-1,3-dienyl)zirconium are dissolved in 100 ml of toluene, admixed with a solution of 10 mmol of acetylacetone in 50 ml of toluene and stirred for 10 hours at room temperature. The solvent is subsequently removed in an oil pump vacuum and the remaining pale brown solid is redissolved in as little toluene as possible. A similar amount of pentane is added and the solution is stored for two days at 4° C. to precipitate the product. The supernatant solvent is then decanted off and the remaining yellow powder is washed with a little pentane and dried in an oil pump vacuum. This gives [Tris(pentafluorophenyl)(η⁵-cyclopentadienylidene)borato](η⁵-cyclopentadienyl)acetylacetonatozirconium in a yield of 76%.

EXAMPLE 4

[Tris(pentafluorophenyl)(η⁵-cyclopentadienylidene)borato](η⁵-cyclopentadienyl)methylzirconium 1.6 ml of AlMe₃ (16 mmol) are syphoned into a solution of 0.5 mmol of [tris(pentafluorophenyl)(η⁵-cyclopentadienylidene)borato](η⁵-cyclopentadienyl)acetylacetonatozirconium in 35 ml of toluene. The pale yellow solution becomes orange after 10 minutes. The mixture is then stirred for a further 2 hours at room temperature and 15 ml of diethyl ether are added to deactivate excess AlMe₃. The solution is evaporated to dryness and the red oil obtained is washed once with 20 ml of pentane. This gives an orange-red solid in a yield of 83%.

We claim:

1. A transition metal compound of the formula I $$L_n(X_mA_tR^1_q)_sMY_r \qquad (1),$$

where

M is a metal atom of group IIIb, IVb, Vb or VIb of the Periodic Table of the Elements, L are identical or different and are each a η ligand or an electron donor, n is 1,2, 3 or 4, Y are, independently of one another, identical or different and are each a hydrogen atom, a halogen atom or an l-dentate $C_1$–$C_{40}$-group, where I is 1,2, 3 or 4, r is 0, 1,2,3 or 4 and at least one of the radicals L bears at least one group $X_mA_tR^1_q$, where X are identical or different and are each a hetero atom or a $C_1$–$C_{40}$-group, m is 0 or or 1, A is a tetravalent atom of group IIIa of the Periodic Table of the Elements, t is 1, $R^1$ are identical are each a $C_1$–$C_{40}$-group, q is 3 and s is an integer from 1 to 20.

2. A transition metal compound of the formula I as claimed in claim 1, wherein L are identical or different and are unsubstituted or substituted cyclopentadienyl groups.

3. A transition metal compound of the formula I as claimed in claim 1, wherein L are identical or different and are substituted or unsubstituted indenyl groups.

4. A transition metal compound of the formula I as claimed in claim 1, wherein n is 2 and the two radicals L are connected to one another via a bridge Z.

5. A transition metal compound of the formula I as claimed in claim 4, wherein the bridge Z is $$-M^2-, \quad -M^2-M^2-, \quad -\underset{R^3}{\overset{R^2}{C}}-\underset{R^3}{\overset{R^2}{C}}-, \quad -\underset{R^3}{\overset{R^2}{M^2}}-\left[\underset{R^3}{\overset{R^2}{C}}\right]_x \underset{R^3}{\overset{R^2}{M^2}}-,$$

$$-O-\underset{R^3}{\overset{R^2}{M^2}}-O-, \quad -\underset{R^3}{\overset{R^2}{C}}-, \quad -O-\underset{R^3}{\overset{R^2}{M^2}}-, \quad -\underset{R^3}{\overset{R^2}{C}}-\underset{R^3}{\overset{R^2}{M^2}}-,$$

$$-\underset{R^3}{\overset{R^2}{C}}-\underset{R^3}{\overset{R^2}{C}}-\underset{R^3}{\overset{R^2}{C}}-, \quad \underset{/}{\overset{\backslash}{B}}R^2, \quad \underset{/}{\overset{\backslash}{Al}}R^2, \quad -Ge-, \quad -O-, \quad -S-,$$

$$\underset{/}{\overset{\backslash}{S}}O, \quad \underset{/}{\overset{\backslash}{S}}O_2, \quad \underset{/}{\overset{\backslash}{N}}R^2, \quad \underset{/}{\overset{\backslash}{C}}O, \quad \underset{/}{\overset{\backslash}{P}}R^2 \text{ or } \underset{/}{\overset{\backslash}{P}}(O)R^2,$$

where $R^2$ and $R^3$ are identical or different and are each a hydrogen atom, a halogen atom or a $C_1$–$C_{40}$-group of $R^2$ and $R^3$ together with the atoms connecting them form one or more rings and $R^2$ or/and $R^3$ can be bound to L, x is an interger from zero to 18, and $M^2$ is silicon, germanium or tin.

6. A transition metal compound of the formula I as claimed in claim 5, wherein $R^2$ and $R^3$ are identical or different and are each a $C_1$–$C_2$ alkyl or a $C_6$–$C_{10}$ aryl and x is 6.

7. A transition metal compound of the formula I as claimed in claim 1, wherein Y are saturated or unsaturated, linear, cyclic or branched and are each a $C_1$–$C_{20}$-alkyl group, a $C_1$–$C_{20}$-haloalkyl group, a $C_6$–$C_{20}$-aryl group, a $C_6$–$C_{20}$-haloaryl group, a $C_2$–$C_{40}$-alkenyl group, a $C_7$–$C_{40}$-arylalkyl group, a $C_7$–$C_{40}$-alkylaryl group or a $C_8$–$C_{40}$-arylalkenyl group, each of which optionally contain silicon, germanium, tin, oxygen, nitrogen, sulfur or phosphorus.

8. A transition metal compound of the formula I as claimed in claim 1, wherein X are saturated or unsaturated, linear, cyclic or branched and are each a $C_1$–$C_{20}$-alkylene group, a $C_6$–$C_{20}$-arylene group, a $C_2$–$C_{20}$-alkenylene group, a $C_7$–$C_{40}$-arylalkylene group, a $C_7$–$C_{40}$-alkylarylene group or a $C_8$–$C_{40}$-arylalkenylene group, each of which optionally contain silicon, germanium or tin.

9. A transition metal compound of the formula I as claimed in claim 1, wherein $R^1$ are saturated or unsaturated, linear, cyclic or branched and are each a $C_1$–$C_{20}$-alkyl group, a $C_1$–$C_{20}$-haloalkyl group, a $C_6$–$C_{20}$-aryl group, a $C_6$–$C_{20}$-haloaryl group, a $C_2$–$C_{20}$-alkenyl group, a $C_7$–$C_{40}$-arylalkyl group, a $C_7$–$C_{40}$-alkylaryl group or a $C_8$–$C_{40}$-arylalkenyl group.

10. A transition metal compound of the formula I as claimed in claim 1, wherein

M is titanium, zirconium or hafnium, n is 2,

L are identical or different and are each a substituted or unsubstituted cyclopentadienyl group, where two radicals L optionally are connected to one another via a bridge Z, where z is $CR^2R^3$ or $SiR^2R^3$ or a unit Si—$(CR^2R^3)_x$—Si which links two groups $L_n(X_mA_tR^1_q)_sMY_r$ with one another, where $R^2$ and $R^3$ are identical or different and are each a $C_1$–$C_{20}$-hydrocarbon group and x is an integer from 0 to 10, Y is a monodentate or bidentate, three- to six-membered carbon-containing group which is saturated or unsaturated and optionally is substituted by $C_1$–$C_{40}$-groups, r is 1 or 2, X is a $C_1$–$C_{20}$-hydrocarbon group, where m is 0 or 1, $R^1$ are identical or different and are each a perhalogenated $C_1$–$C_{20}$-group, and s is 1,2, 3 or 4.

11. A transition metal compound of the formula I as claimed in claim 1, wherein

M is zirconium, n is 2,

L are identical or different and are each a substituted cyclopentadienyl group, where two radicals L are connected to one another via a bridge Z, where Z is $CR^2R^3$ or $SiR^2R^3$, where $R^2$ and $R^3$ are identical or different and are $C_1$–$C_{10}$-alkyl or $C_6$–$C_{10}$-aryl, Y is a monodentate unsaturated $C_5$-hydrocarbon group which is optionally substituted by $C_1$–$C_{10}$-alkyl groups, r is 1, m is 0, A is a boron atom or an aluminum atom, t is 1, $R^1$ are identical and are each a pentafluorophenyl group $(C_6F_5)$ and q is 3, and s is 1 or 2.

12. The transition metal compound of the formula I as claimed in claim 1, wherein A is boron n is 2 and the two radicals L are connected to one another via a bridge Z.

13. A transition metal compound selected from the group consisting of

[tris(pentafluorophenyl)(cyclopentadienylidene)borato] (cyclopentadienyl)-1,2,3-trimethylpenta-1,3-dienylzirconium, [tris(pentafluorophenyl) (methylcyclopentadienylidene)borato] (methylcyclopenta-dienyl)-1,2,3-trimethylpenta-1,3-dienylzirconium, [tris(pentafluorophenyl)(n-butylcyclopentadienylidene)borato](n-butylcyclopentadienyl)-1,2,3-trimethylpenta-1,3-dienylzirconium, [tris(pentafluorophenyl)(indenylidene) borato](indenyl)-1,2,3-trimethylpenta-1,3-dienylzirconium, [tris(pentafluorophenyl) (cyclopentadienylidene)borato](tert-butylamido) dimethylsilane-1,2,3-trimethylpenta-1,3-dienylzirconium, [tris(pentafluorophenyl)(2-methylbenzindenylidene)borato](2-methylbenzindenyl)1,2,3-trimethylpenta-1,3-dienylzirconium, dimethylsilanediyl-[tris(pentafluorophenyl)(2-methylindenylidene)borato](2-methylindenyl)-1,2,3-trimethylpenta-1,3-dienylzirconium, dimethylsilanediyl-[tris(pentafluorophenyl)(indenylidene)borato](indenyl)-1,2,3-trimethylpenta-1,3-dienylzirconium, dimethylsilanediyl-[tris(pentafluorophenyl)(2-methylbenzindenylidene)borato](2-methylbenzindenyl)-1,2,3-trimethylpenta-1,3-dienylzirconium, dimethylsilanediyl-[tris(pentafluorophenyl)(2- methylindenylidene)borato](2-methylbenzindenyl)-1,2,3-trimethylpenta-1,3-dienylzirconium, dimethylsilanediyl-[tris(pentafluorophenyl)(2-methylbenzindenylidene)borato](2-methyl-4-phenylindenyl)-1,2,3-trimethylpenta-1,3-dienylzirconium, dimethylsilanediyl-[tris(pentafluorophenyl)(2-methylindenylidene)borato](4-phenylindenyl)-1,2,3-trimethylpenta-1,3-dienylzirconium, dimethylsilanediyl-[tris(pentafluorophenyl)(2-methyl-4-phenylindenylidene)borato](2-methyl-4-phenylindenyl)-1,2,3-trimethylpenta-1,3-dienylzirconium, dimethylsilanediyl-[tris(pentafluorophenyl)(2-methyl-4,6-diisopropylindenylidene)borato](2-methyl-4,6-diisopropylindenyl)-1,2,3-trimethylpenta-1,3-dienylzirconium, dimethylsilanediyl-[tris(pentafluorophenyl)(2-methyl-4-naphthylindenylidene)borato](2-methyl-4-naphthylindenyl)-1,2,3-trimethylpenta-1,3-dienylzirconium, isopropylidene-[tris(pentafluorophenyl)(cyclopentadienylidene)borato](fluorenyl)-1,2,3-trimethylpenta-1,3-dienylzirconium, isopropylidene[tris(pentafluorophenyl)(cyclopentadienylidene)borato](indenyl)-1,2,3-trimethylpenta-1,3-dienylzirconium, [tris(pentafluorophenyl)(cyclopentadienylidene)borato](-4,7,7-trimethyl-(4,5,6,7-tetrahydroindenyl)-1,2,3-trimethylpenta-1,3-dienylzirconium, [tris(trifluoromethyl)(cyclopentadienylidene)borato](cyclopentadienyl)-1,2,3-trimethylpenta-1,3-dienylzirconium, [tris(trifluoromethyl)(methylcyclopentadienylidene)borato](methylcyclopentadienyl)-1,2,3-trimethylpenta-1,3-dienylzirconium [tris(trifluoromethyl)(n-butylcyclopentadienylidene)borato](n-butylcyclopentadienyl)-1,2,3-trimethylpenta-1,3-dienylzirconium, [tris(trifluoromethyl)(indenylidene)borato](indenyl)-1,2,3-trimethylpenta-1,3-dienylzirconium, [tris(trifluoromethyl)(cyclopentadienylidene)borato](tert-butylamido)dimethylsilane-1,2,3-trimethylpenta-1,3-dienylzirconium, [tris(trifluoromethyl)(2-methylbenzindenylidene)borato](2-methylbenzindenyl)-1,2,3-trimethylpenta-1,3-dienylzirconium, dimethylsilanediyl-[tris(trifluoromethyl)(2-methylindenylidene)borato](2-methylindenyl)-1,2,3-trimethylpenta-1,3-dienylzirconium, dimethylsilanediyl [tris(trifluoromethyl)(indenylidene)borato](indenyl)1,2,3-trimethylpenta-1,3-dienylzirconium, dimethylsilanediyl-[tris(trifluoromethyl)(2-methylbenzindenylidene)borato](2-methylbenzindenyl)-1,2,3-trimethylpenta-1,3-dienylzirconium, dimethylsilanediyl-[tris(trifluoromethyl)(2-methylindenylidene)borato](2-methylbenzindenyl)-1,2,3-trimethylpenta-1,3-dienylzirconium, dimethylsilanediyl-[tris(trifluoromethyl)(2-methylbenzindenylidene)borato](2-methyl-4-phenylindenyl)1,2,3-trimethylpenta-1,3-dienylzirconium, dimethylsilanediyl-[tris(trifluoromethyl)(2-methylindenylidene)borato](4-phenylindenyl)-1,2,3-trimethylpenta-1,3-dienylzirconium, dimethylsilanediyl-[tris(trifluoromethyl)(2-methyl-4-phenylindenylidene)borato](2-methyl-4-phenylindenyl)-1,2,3-trimethylpenta-1,3-dienylzirconium, dimethylsilanediyl-[tris(trifluoromethyl)(2-methyl-4,6-diisopropylindenylidene)borato](2-methyl-4,6-diisopropylindenyl)-1,2,3-trimethylpenta-1,3-dienylzirconium, dimethylsilanediyl-[tris(trifluoromethyl)(2-methyl-4-naphthylindenylidene)borato](2-methyl-4lindenyliden)borato](2-methyl-4-napthylindenyl-1,2,3-trimethylpenta-1,3-dienylzirconium, isopropylidene[tris(trifluoromethyl)(cyclopentadienylidene)borato](fluorenyl)-1,2,3-trimethylpenta-1,3-dienylzirconium, isopropylidene[tris(trifluoromethyl)(cyclopentadienylidene)borato](indenyl)-1,2,3-trimethylpenta-1,3-dienylzirconium, [tris(trifluoromethyl)(cyclopentadienylidene)borato](-4,7,7-trimethyl-(4,5,6,7-tetrahydroindenyl)-1,2,3-trimethylpenta-1,3-dienylzirconium, methylphenylmethylene[tris(pentafluorophenyl)(cyclopentadienylidene)borato](fluorenyl)-1,2,3-trimethylpenta-1,3-dienylzirconiumn, diphenylmethylene[tris(pentafluorophenyl)(cyclopentadienylidene)borato](fluorenyl)-1,2,3-trimethylpenta-1,3-dienylzirconium, isopropylidene-[tris(pentafluorophenyl)(3-methylcyclopentadienylidene)borato](fluorenyl)-1,2,3-trimethylpenta-1,3-dienylzirconium, dimethylsilanediyl-[tris(pentafluorophenyl)(-3-(tert-butylcyclopentadienylidene)borato]-(fluorenyl)-1,2,3-trimethylpenta-1,3-dienylzirconium, diphenylsilanediyl-[tris(pentafluorophenyl)(-3-(trimethylsilyl)cyclopentadienylidene)borato]-(fluorenyl)-1,2,3-trimethylpenta-1,3-dienylzirconium, methylphenylsilanediyl-[tris(pentafluorophenyl)(2-methylindenylidene)borato](2-methylindenyl)1,2,3-trimethylpenta-1,3-dienylzirconium, methylphenylsilanediyl[tris(pentafluorophenyl)(indenylidene)borato](indenyl)-1,2,3-trimethylpenta-1,3-dienylzirconium, methylphenylsilanediyl-[tris(pentafluorophenyl)(2-methyl-4,5-benzindenylidene)borato](2-methyl-4,5-benzindenyl)-1,2,3-trimethylpenta-1,3-dienylzirconium, methylphenylsilanediyl-[tris(pentafluorophenyl)(2-methylindenylidene)borato](2-methyl-4,5-benzindenyl)-1,2,3-trimethylpenta-1,3-dienylzirconium, methylphenylsilanediyl-[tris(pentafluorophenyl)(2-methyl-4,5-benzindenylidene)borato](2-methyl-4-phenylindenyl)-1,2,3-trimethylpenta-1,3-dienylzirconium, methylphenylsilanediyl-[tris(pentafluorophenyl)(2-methylindenylidene)borato](4-phenylindenyl)-1,2,3-trimethylpenta-1,3-dienylzirconium, methylphenylsilanediyl-[tris(pentafluorophenyl)(2-methyl-4-phenylindenylidene)borato](2-methyl-4-phenylindenyl)-1,2,3-trimethylpenta-1,3-dienylzirconium, methylphenylsilanediyl-[tris(pentafluorophenyl)(2-ethyl-4-phenylindenylidene)borato](2-ethyl-4-phenylindenyl)-1,2,3-trimethylpenta-1,3-dienylzirconium, methylphenylsilanediyl-[tris(pentafluorophenyl)(2-methyl-4,6-diisopropylindenylidene)-borato](2-methyl-4,6-diisopropylindenyl)-1,2,3-trimethylpenta-1,3-dienylzirconium, methylphenylsilanediyl-[tris(pentafluorophenyl)(2-methyl-4-naphthylindenylidene)-borato](2-methyl-4-naphthylindenyl-1,2,3-trimethylpenta-1,3-dienylzirconium, ethylene-[tris(pentafluorophenyl)(indenylidene)borato](indenyl)-1,2,3-trimethylpenta-1,3-dienylzirconium, ethylene-[tris(pentafluorophenyl)(2-methylindenylidene)borato](2-methylindenyl)-1,2,3-trimethylpenta-1,3-dienylzirconium, ethylene-[tris(pentafluorophenyl)(2-methyl-4,5-benzindenylidene)borato](2-methyl-4,5-benzindenyl)-1,2,3-trimethylpenta-1,3-dienylzirconium, ethylene-[tris(pentafluorophenyl)(2-methylindenylidene)borato](2-methyl-4,5-benzindenyl)-1,2,3-trimethylpenta-1,3-dienylzirconium, ethylene-[tris(pentafluorophenyl)(2-methyl-4,5-benzindenylidene)borato](2-methyl-4-phenylindenyl)-1,2,3-trimethylpenta-1,3-dienylzirconium, ethylene-[tris(pentafluorophenyl)(2- methylindenylidene)borato](4-phenylindenyl)-1,2,3-trimethylpenta-1,3-dienylzirconium, ethylene-[tris(pentafluorophenyl)(2-methyl-4-phenylindenylidene)borato](2-methyl-4-phenylindenyl)-1,2,3-trimethylpenta-1,3-dienylzirconium, ethylene-[tris(pentafluorophenyl)(2-methyl-4,6-diisopropylindenylidene)borato](2-methyl-4,6-diisopropylindenyl)-1,2,3-trimethylpenta-1,3-dienylzirconium, ethylene-[tris(pentafluorophenyl)(2-methyl-4-naphthylindenylidene)borato](2-methyl-4-naphthylindenyl)-1,2,3-trimethylpenta-1,3-dienylzirconium, ethylene-[tris(pentafluorophenyl)(2-ethyl-4-phenylindenylidene)borato](2-ethyl-4-phenylindenyl)-1,2,3-trimethylpenta-1,3-dienylzirconium, [bis(pentafluorophenyl)(cyclopentadienylidene)borane](cyclopentadienyl)-1,2,3-trimethylpenta-1,3-dienylzirconium, [bis(pentafluorophenyl)(methylcyclopentadienylidene)borane](methylcyclopenta-dienyl)-1,2,3-trimethylpenta-1,3-dienylzirconium, [bis(pentafluorophenyl)(n-butylcyclopentadienylidene)borane](n-butylcyclopentadienyl)-1,2,3-trimethylpenta-1,3-dienylzirconium, [bis(pentafluorophenyl)(indenylidene)borane](indenyl)-1,2,3-trimethylpenta-1,3-dienylzirconium, [bis(pentafluorophenyl)(cyclopentadienylidene)borane](tert-butylamido)dimethylsilane-1,2,3-trimethylpenta-1,3-dienylzirconium, [bis(pentafluorophenyl)(2-methylbenzindenylidene)borane](2-methylbenzindenyl)-1,2,3-trimethylpenta-1,3-dienylzirconium, dimethylsilanediyl-[bis(pentafluorophenyl)(2-methylindenylidene)borane](2-methylindenyl)-1,2,3-trimethylpenta-1,3-dienylzirconium, dimethylsilanediyl[bis(pentafluorophenyl)(indenylidene)borane](indenyl)-1,2,3-trimethylpenta-1,3-dienylzirconium, dimethylsilanediyl-[bis(pentafluorophenyl)(2-methylbenzindenylidene)borane](2-methylbenzindenyl)-1,2,3-trimethylpenta-1,3-dienylzirconium, dimethylsilanediyl-[bis(pentafluorophenyl)(2-methylbenzindenylidene)borane](2-methylbenzindenyl)-1,2,3-trimethylpenta-1,3-dienylzirconium, dimethylsilanediyl-[bis(pentafluorophenyl)(2-methylbenzindenylidene)borane](2-methyl-4-phenylindenyl)-1,2,3-trimethylpenta-1,3-dienylzirconium, dimethylsilanediyl-[bis(pentafluorophenyl)(2-methylindenylidene)borane](4-phenylindenyl)-1,2,3-trimethylpenta-1,3-dienylzirconium, dimethylsilanediyl-[bis(pentafluorophenyl)(2-methyl-4-phenylindenylidene)borane](2-methyl-4-phenylindenyl)-1,2,3-trimethylpenta-1,3-dienylzirconium, dimethylsilanediyl-[bis(pentafluorophenyl)(2-methyl-4,6-diisopropylindenylidene)borane](2-methyl-4,6-diisopropylindenyl)-1,2,3-trimethylpenta-1,3-dienylzirconium, dimethylsilanediyl-[bis(pentafluorophenyl)(2-methyl-4-naphthylindenylidene)borane](2-methyl-4-naphthylindenyl)-1,2,3-trimethylpenta-1,3-dienylzirconium, isopropylidene[bis(pentafluorophenyl)(cyclopentadienylidene)borane](fluorenyl)1,2,3-trimethylpenta-1,3-dienylzirconium, isopropylidene[bis(pentafluorophenyl)(cyclopentadienylidene)borane](indenyl)-1,2,3-trimethylpenta-1,3-dienylzirconium, [bis(pentafluorophenyl)(cyclopentadienylidene)borane](4,7,7-trimethyl-(4,5,6,7,-tetrahydroindenyl)-1,2,3-trimethylpenta-1,3-dienylzirconium, [bis(trifluoromethyl)(cyclopentadienylidene)borane](cyclopentadienyl)-1,2,3-trimethylpenta-1,3-dienylzirconium, [bis(trifluoromethyl)(methylcyclopentadienylidene)borane](methylcyclopentadienyl)-1,2,3-trimethylpenta-1,3-dienylzirconium, [bis(trifluoromethyl)(n-butylcyclopentadienylidene)borane](n-butylcyclopentadienyl)-1,2,3-trimethylpenta-1,3-dienylzirconium, [bis(trifluoromethyl)(indenylidene)borane](indenyl)-1,2,3-trimethylpenta-1,3-dienylzirconium, [bis(trifluoromethyl)(cyclopentadienylidene)borane](tert-butylamido)dimethylsilane-1,2,3-trimethylpenta-1,3-dienylzirconium, [bis(trifluoromethyl)(2-methylbenzindenylidene)borane](2-methylbenzindenyl)-1,2,3-trimethylpenta-1,3-dienylzirconium, dimethylsilanediyl-[bis(trifluoromemethyl)(2-methylindenylidene)borane](2-methylindenyl)-1,2,3-trimethylpenta-1,3-dienylzirconium, dimethylsilanediyl[bis(trifluoromethyl)(indenylidene)borane](indenyl)-1,2,3-trimethylpenta-1,3-dienylzirconium, dimethylsilanediyl-[bis(trifluoromethyl)(2-methylbenzindenylidene)borane](2-methylbenzindenyl)-1,2,3-trimethylpenta-1,3-dienylzirconium, dimethylsilanediyl-[bis(trifluoromethyl)(2-methylbenzindenylidene)borane](2-methylbenzindenyl)-1,2,3-trimethylpenta-1,3-dienylzirconium, dimethylsilanediyl-[bis(trifluoromethyl)(2-methylbenzindenylidene)borane](2-methyl-4-phenylindenyl)-1,2,3-trimethylpenta-1,3-dienylzirconium, dimethylsilanediyl-[bis(trifluoromethyl)(2-methylindenylidene)borane](4-phenylindenyl)-1,2,3-trimethylpenta-1,3-dienylzirconium, dimethylsilanediyl-[bis(trifluoromethyl)(2-methyl-4-phenylindenylidene)borane](2-methyl-4-phenylindenyl)-1,2,3-trimethylpenta-1,3-dienylzirconium, dimethylsilanediyl-[bis(trifluoromethyl)(2-methyl-4,6-diisopropylindenylidene)borane](2-methyl-4,6-diisopropylindenyl)-1,2,3-trimethylpenta-1,3-dienylzirconium, dimethylsilanediyl-[bis(trifluoromethyl)(2-methyl-4-naphthylindenylidene)borane](2-methyl-4-naphthylindenyl)-1,2,3-trimethylpenta-1,3-dienylzirconium, isopropylidene[bis(trifluoromethyl)(cyclopentadienylidene)borane](fluorenyl)-1,2,3-trimethylpenta-1,3-dienylzirconium, isopropylidene[bis(trifluoromethyl)(cyclopentadienylidene)borane](indenyl)-1,2,3-trimethylpenta-1,3-dienylzirconium, [bis(trifluoromethyl)(cyclopentadienylidene)borane](4,7,7-trimethyl-(4,5,6,7,-tetrahydroindenyl)-1,2,3-trimethylpenta-1,3-dienylzirconium, methylphenylmethylene-[bis(pentafluorophenyl)(cyclopentadienylidene)borane](fluorenyl)-1,2,3-trimethylpenta-1,3-dienylzirconium, diphenylmethylene[bis(pentafluorophenyl)(cyclopentadienylidene)borane](fluorenyl)-1,2,3-trimethylpenta-1,3-dienylzirconium, isopropylidene-[bis(pentafluorophenyl)(3-methylcyclopentadienylidene)borane](fluorenyl)-1,2,3-trimethylpenta-1,3-dienylzirconium, dimethylsilanediyl-[bis(pentafluorophenyl)(3-(tert-butylcyclopentadienylidene)borane](fluorenyl)-1,2,3-trimethylpenta-1,3-dienylzirconium, diphenylsilanediyl-[bis(pentafluorophenyl)(3-(trimethylsilyl)cyclopentadienylidene)borane](fluorenyl)-1,2,3-trimethylpenta-1,3-dienylzirconium, methylphenylsilanediyl-[bis(pentafluorophenyl)(2-methylindenylidene)borane](2-methylindenyl)-1,2,3-trimethylpenta-1,3-dienylzirconium, methylphenylsilanediyl[bis(pentafluorophenyl)(indenylidene)borane](indenyl)-1,2,3-trimethylpenta-1,3-dienylzirconium, methylphenylsilanediyl-[bis(pentafluorophenyl)(2-methyl-4,5-benzindenylidene)borane](2-methyl-4,5-benzindenyl)-1,2,3-trimethylpenta-1,3-dienylzirconium, methylphenylsilanediyl-[bis(pentafluorophenyl)(2-methylindenylidene)borane](2-methyl-4,5-benzindenyl)-1,2,3-trimethylpenta-1,3-dienylzirconium, methylphenylsilanediyl-[bis(pentafluorophenyl)(2-methyl-4,5-benzindenylidene)borane](2-methyl-4-phenylindenyl)-1,2,3-trimethylpenta-1,3-dienylzirconium, methylphenylsilanediyl-[bis(pentafluorophenyl)(2-methylindenylidene)borane](4-phenylindenyl)-1,2,3-trimethylpenta-1,3-dienylzirconium, methylphenylsilanediyl-[bis(pentafluorophenyl)(2-methyl-4-phenylindenylidene)borane](2-methyl-4-phenylindenyl)-1,2,3-trimethylpenta-1,3-dienylzirconium, methylphenylsilanediyl-[bis(pentafluorophenyl)(2-ethyl-4-phenylindenylidene)borane](2-ethyl-4-phenylindenyl)-1,2,3-trimethylpenta-1,3-dienylzirconium, methylphenylsilanediyl-[bis(pentafluorophenyl)(2-methyl-4,6-diisopropylindenylidene)borane](2-methyl-4,6-diisopropylindenyl)-1,2,3-trimethylpenta-1,3-dienylzirconium, methylphenylsilanediyl-[bis(pentafluorophenyl)(2-methyl-4-naphthyl-indenylidene)borane](2-methyl-4-naphthylindenyl)-1,2,3-trimethylpenta-1,3-dienylzirconium, ethylene-[bis(pentafluorophenyl)(indenylidene)borane](indenyl)-1,2,3-trimethylpenta-1,3-dienylzirconium, ethylene-[bis(pentafluorophenyl)(2-methylindenylidene)borane](2-methylindenyl)-1,2,3-trimethylpenta-1,3-dienylzirconium, ethylene-[bis(pentafluorophenyl)(2-methyl-4,5-benzindenylidene)borane](2-methyl-4,5-benzindenyl)-1,2,3-trimethylpenta-1,3-dienylzirconium, ethylene-[bis(pentafluorophenyl)(2-methylindenylidene)borane](2-methyl-4,5-benzindenyl)-1,2,3-trimethylpenta-1,3-dienylzirconium, ethylene-[bis(pentafluorophenyl)(2-methyl-4,5-benzindenylidene)borane](2-methyl-4-phenylindenyl)-1,2,3-trimethylpenta-1,3-dienylzirconium, ethylene-[bis(pentafluorophenyl)(2-methylindenylidene)borane](4-phenylindenyl)-1,2,3-trimethylpenta-1,3-dienylzirconium, ethylene-[bis(pentafluorophenyl)(2-methyl-4-phenyl-indenylidene)borane](2-methyl-4-phenylindenyl)-1,2,3-trimethylpenta-1,3-dienylzirconium, ethylene-[bis(pentafluorophenyl)(2-methyl-4,6-diisopropyl-indenylidene)borane](2-methyl-4,6-diisopropylindenyl)-1,2,3-trimethylpenta-1,3-dienylzirconium, ethylene-[bis(pentafluorophenyl)(2-methyl-4-naphthyl-indenylidene)borane](2-methyl-4-naphthylindenyl)-1 2,3-trimethylpenta-1,3-dienylzirconium, ethylene-[bis(pentafluorophenyl)(2-ethyl-4-phenyl-indenylidene)borane](2-ethyl-4-phenylindenyl)-1,2,3-trimethylpenta-1,3-dienylzirconium,

[tris(pentafluorophenyl)(cyclopentadienylidene)borato](cyclopentadienyl)-1,2,3,4-tetraphenylbuta-1,3-dienylzirconium, [tris(pentafluorophenyl)(2-methylbenzindenylidene)borato](2-methylbenzindenyl)-1,2,3,4-tetraphenylbuta-1,3-dienylzirconium, dimethylsilanediyl-[tris(pentafluorophenyl)(2-methyl-indenylidene)borato](2-methyl-indenyl)-1,2,3,4-tetraphenylbuta-1,3-dienylzirconium, dimethylsilanediyl-[tris(pentafluorophenyl)(2-methylbenzindenylidene)borato](2-methyl-4-phenylindenyl)-1,2,3,4-tetraphenylbuta-1,3-dienylzirconium, dimethylsilanediyl-[tris(pentafluorophenyl)(2-methyl-4-phenylindenylidene)borato](2-methyl-4-phenylindenyl)-1,2,3,4-tetraphenylbuta-1,3-dienylzirconium, dimethylsilanediyl-[tris(pentafluorophenyl)(2-methyl-4-naphthylindenylidene)borato](2-methyl-4-naphthylindenyl)-1,2,3,4-tetraphenylbuta-1,3-dienylzirconium, isopropylidene-[tris(pentafluorophenyl)(cyclopentadienylidene)borato](fluorenyl)-1,2,3,4-tetraphenylbuta-1,3-dienylzirconium, dimethylsilanediyl-[tris(trifluoromethyl)(2-methylbenzindenylidene)borato](2-methylbenzindenyl-)-1,2,3,4-tetraphenylbuta-1,3-dienylzirconium, dimethylsilanediyl-[tris(trifluoromethyl)(2-methyl-4-phenylindenylidene)borato](2-methyl-4-phenylindenyl)-1,2,3,4-tetraphenylbuta-1,3-dienylzirconium, dimethylsilanediyl-[tris(trifluoromethyl)(2-methyl-4,6-diisopropylindenylidene)borato](2-methyl-4,6-diisopropylindenyl)-1,2,3,4-tetraphenylbuta-1,3-dienylzirconium, methylphenylmethylene-[tris(pentafluorophenyl)(cyclopentadienylidene)borato](fluorenyl)-1,2,3,4-tetraphenylbuta-1,3-dienylzirconium, methylphenylsilanediyl-[tris(pentafluorophenyl)(2-methyl-4,5-benzindenylidene)borato](2-methyl-4,5-benzindenyl)-1,2,3,4-tetraphenylbuta-1,3-dienylzirconium, methylphenylsilanediyl-[tris(pentafluorophenyl)(2-ethyl-4-phenylindenylidene)borato](2-ethyl-4-phenylindenyl)-1,2,3,4-tetraphenylbuta-1,3-dienylzirconium, ethylene-[tris(pentafluorophenyl)(2-methylindenylidene)borato](2-methylindenyl)-1,2,3,4-tetraphenylbuta-1,3-dienylzirconium, [tris(pentafluorophenyl)(cyclopentadienylidene)borato](cyclopentadienyl)-1-methyl-2,3-cyclohexylene-penta-1,3-dienylzirconium, dimethylsilanediyl-[tris(pentafluorophenyl)(2-methyl-4-phenylindenylidene)borato](2-methyl-4-phenylindenyl)1-methyl-2,3-cyclohexylene-penta-1,3-dienylzirconium, [tris(pentafluorophenyl)(cyclopentadienylidene)borato](cyclopentadienyl)-1,4-di(trimethylsilyl)-2,3-dimethylbuta-1,3-dienylzirconium, dimethylsilanediyl-[tris(pentafluorophenyl)(2-methyl-4-phenylindenylidene)borato](2-methyl-4-phenylindenyl)-1,4-di(trimethylsilyl)-2,3-dimethylbuta-1,3-dienylzirconium, [tris(pentafluorophenyl)(cyclopentadienylidene)borato](cyclopentadienyl)acetylacetonatozirconium, dimethylsilanediyl-[tris(pentafluorophenyl)(2-methyl-4-phenylindenylidene)borato](2-methyl-4-phenylindenyl)acetylacetonatozirconium, [tris(pentafluorophenyl)(cyclopentadienylidene)borato](cyclopentadienyl)bipyridylzirconium, dimethylsilanediyl-[tris(pentafluorophenyl)(2-methyl-4-phenylindenylidene)borato](2-methyl-4-phenylindenyl)bipyridylzirconium, [tris(pentafluorophenyl)(cyclopentadienylidene)borato](cyclopentadienyl)chlorozirconium, dimethylsilanediyl[tris(pentafluorophenyl)(2-methyl-4-phenylindenylidene)borato](2-methyl-4-phenylindenyl)chlorozirconium, [tris(pentafluorophenyl)(cyclopentadienylidene)borato]bis(cyclopentadienyl)zirconium, [tris(pentafluorophenyl)(2-methylbenzindenylidene)borato](2-methylbenzindenyl)methylzirconium, dimethylsilanediyl[tris(pentafluorophenyl)(2-methyl-4-phenylindenylidene)borato](2-methylindenyl)methylzirconium, dimethylsilanediyl[tris(pentafluorophenyl)(2-methylbenzindenylidene)borato](2-methyl-4-phenylindenyl)methylzirconium, dimethylsilanediyl[tris(pentafluorophenyl)(2-methyl-4-naphthylindenylidene)borato](2-methyl-4-naphthylindenyl)methylzirconium, isopropylidene-[tris(pentafluorophenyl)(cyclopentadienylidene)borato]

(fluorenyl)methylzirconium, dimethylsilanediyl[tris(trifluoromethyl)(2-methylbenzindenylidene)borato](2-methylbenzindenyl)methylzirconium, dimethylsilanediyl[tris(trifluoromethyl)(2-methyl-4-phenylindenylidene)borato](2-methyl-4-phenylindenyl)methylzirconium, dimethylsilanediyl[tris(trifluoromethyl)(2-methyl-4,6-diisopropylindenylidene)borato](2-methyl-4,6-diisopropylindenyl)methylzirconium, methylphenylmethylene[tris(pentafluorophenyl)(cyclopentadienylidene)borato](fluorenyl)methylzirconium, methylphenylsilanediyl[tris(pentafluorophenyl)(2-methyl-4,5-benzindenylidene)borato](2-methyl-4,5-benzindenyl)methylzirconium, methylphenylsilanediyl[tris(pentafluorophenyl)(2-ethyl-4-phenyl-indenylidene)borato](2-ethyl-4-phenylindenyl)methylzirconium, ethylene[tris(pentafluorophenyl)(2-methylindenylidene)borato](2-methylindenyl)methylzirconium, [tris(pentafluorophenyl)(2-methylbenzindenylidene)borato](2-methylbenzindenyl)phenylzirconium, dimethylsilanediyl[tris(pentafluorophenyl)(2-methylindenylidene)borato](2-methylindenyl)phenylzirconium, dimethylsilanediyl[tris(pentafluorophenyl)(2-methylbenzindenylidene)borato](2-methyl-4-phenylindenyl)phenylzirconium, dimethylsilanediyl[tris(pentafluorophenyl)(2-methyl-4-naphthylindenylidene)borato](2-methyl-4-naphthylindenyl)phenylzirconium, isopropylidene[tris(pentafluorophenyl)(cyclopentadienylidene)borato](fluorenyl)phenylzirconium, dimethylsilanediyl[tris(trifluoromethyl)(2-methylbenzindenylidene)borato](2-methylbenzindenyl)phenylzirconium, dimethylsilanediyl[tris(trifluoromethyl)(2-methyl-4-phenylindenylidene)borato](2-methyl-4-phenylindenyl)phenylzirconium, dimethylsilanediyl[tris(trifluoromethyl)(2-methyl-4,6-diisopropylindenylidene)borato](2-methyl-4,6-diisopropylindenyl)phenylzirconium, methylphenylmethylene[tris(pentafluorophenyl)(cyclopentadienylidene)borato](fluorenyl)phenylzirconium, methylphenylsilanediyl[tris(pentafluorophenyl)(2-methyl-4,5-benzindenylidene)borato](2-methyl-4,5-benzindenyl)phenylzirconium, methylphenylsilanediyl[tris(pentafluorophenyl)(2-ethyl-4-phenyl-indenylidene)borato](2-ethyl-4-phenylindenyl)phenylzirconium, ethylene[tris(pentafluorophenyl)(2-methylindenylidene)borato](2-methylindenyl)phenylzirconium, [bis(pentafluorophenyl)(cyclopentadienylidene)borane](cyclopentadienyl)-1,2,3,4-tetraphenylbuta-1,3-dienylzirconium, [bis(pentafluorophenyl)(2-methylbenzindenylidene)borane](2-methylbenzindenyl)-1,2,3,4-tetraphenylbuta-1,3-dienylzirconium, dimethylsilanediyl[bis(pentafluorophenyl)(2-methyl-indenylidene)borane](2-methylindenyl)1,2,3,4-tetraphenylbuta-1,3-dienylzirconium, dimethylsilanediyl[bis(pentafluorophenyl)(2-methylbenzindenylidene)borane](2-methyl-4-phenylindenyl)1,2,3,4-tetraphenylbuta-1,3-dienylzirconium, dimethylsilanediyl[bis(pentafluorophenyl)(2-methyl-4-phenylindenylidene)borane](2-methyl-4-phenylindenyl)1,2,3,4-tetraphenylbuta-1,3-dienylzirconium, dimethylsilanediyl[bis(pentafluorophenyl)(2-methyl-4-naphthylindenylidene)borane](2-methyl-4-naphthylindenyl)-1,2,3,4-tetraphenylbuta-1,3-dienylzirconium, isopropylidene[bis(pentafluorophenyl)(cyclopentadienylidene)borane](fluorenyl)-1,2,3,4-tetraphenylbuta-1,3-dienylzirconium, dimethylsilanediyl[bis(trifluoromethyl)(2-methylbenzindenylidene)borane](2-methylbenzindenyl)-1,2,3,4-tetraphenylbuta-1,3-dienylzirconium, dimethylsilanediyl[bis(trifluoromethyl)(2-methyl-4-phenylindenylidene)borane](2-methyl-4-phenylindenyl)-1,2,3,4-tetraphenylbuta-1,3-dienylzirconium, dimethylsilanediyl[bis(trifluoromethyl)(2-methyl-4,6-diisopropylindenylidene)borane](2-methyl-4,6-diisopropylindenyl)-1,2,3,4-tetraphenylbuta-1,3-dienylzirconium, methylphenylmethylene[bis(pentafluorophenyl)(cyclopentadienylidene)borane](fluorenyl)-1,2,3,4-tetraphenylbuta-1,3-dienylzirconium, methylphenylsilanediyl[bis(pentafluorophenyl)(2-methyl-4,5-benzindenylidene)borane](2-methyl-4,5-benzindenyl)-1,2,3,4-tetraphenylbuta-1,3-dienylzirconium, methylphenylsilanediyl[bis(pentafluorophenyl)(2-ethyl-4-phenyl-indenylidene)borane](2-ethyl-4-phenylindenyl)-1,2,3,4-tetraphenylbuta-1,3-dienylzirconium, ethylene[bis(pentafluorophenyl)(2-methylindenylidene)borane](2-methylindenyl)-1,2,3,4-tetraphenylbuta-1,3-dienylzirconium, [bis(pentafluorophenyl)(cyclopentadienylidene)borane](cyclopentadienyl)-1-methyl-2,3-cyclohexylene-penta-1,3-dienylzirconium, dimethylsilanediyl[bis(pentafluorophenyl)(2-methyl-4-phenylindenylidene)borane](2-methyl-4-phenylindenyl)1-methyl-2,3-cyclohexylene-penta-1,3-dienylzirconium, [bis(pentafluorophenyl)(cyclopentadienylidene)borane](cyclopentadienyl)-1,4-di(trimethylsilyl)-2,3-dimethylbuta-1,3-dienylzirconium, dimethylsilanediyl[bis(pentafluorophenyl)(2-methyl-4-phenylindenylidene)borane](2-methyl-4-phenylindenyl)-1,4-di(trimethylsilyl)-2,3-dimethylbuta-1,3-dienylzirconium, [bis(pentafluorophenyl)(cyclopentadienylidene)borane](cyclopentadienyl)acetylacetonatozirconium, dimethylsilanediyl[bis(pentafluorophenyl)(2-methyl-4-phenylindenylidene)borane](2-methyl-4-phenylindenyl)acetylacetonatozirconium, [bis(pentafluorophenyl)(cyclopentadienylidene)borane](cyclopentadienyl)bipyridylzirconium, dimethylsilanediyl[bis(pentafluorophenyl)(2-methyl-4-phenylindenylidene)borane](2-methyl-4-phenylindenyl)bipyridylzirconium, [bis(pentafluorophenyl)(cyclopentadienylidene)borane](cyclopentadienyl)dichlorozirconium, dimethylsilanediyl[bis(pentafluorophenyl)(2-methyl-4-phenylindenylidene)borane](2-methyl-4-phenylindenyl)dichlorozirconium, [bis(pentafluorophenyl)(2-methylbenzindenylidene)borane](2-methylbenzindenyl)dimethylzirconium, dimethylsilanediyl[bis(pentafluorophenyl)(2-methylindenylidene)borane](2-methylindenyl)dimethylzirconium, dimethylsilanediyl[bis(pentafluorophenyl)(2-methylbenzindenylidene)borane](2-methyl-4-phenylindenyl)dimethylzirconium, dimethylsilanediyl[bis(pentafluorophenyl)(2-methyl-4-naphthylindenylidene)borane](2-methyl-4-naphthylindenyl)dimethylzirconium, Isopropylidene[bis(pentafluorophenyl)(cyclopentadienylidene)borane](fluorenyl)dimethylzirconium, dimethylsilanediyl[bis(trifluoromethyl)(2-methylbenzindenylidene)borane](2-methylbenzindenyl)dimethylzirconium, dimethylsilanediyl[bis(trifluoromethyl)(2-methyl-4-phenylindenylidene)borane](2-methyl-4-phenylindenyl)dimethylzirconium, dimethylsilanediyl[bis(trifluoromethyl)(2-methyl-4,6-diisopropylindenylidene)borane](2-methyl-4,6-diisopropylindenyl)dimethylzirconium, methylphenylmethylene[bis(pentafluorophenyl)(cyclopentadienylidene)borane]

(fluorenyl)dimethylzirconium, methylphenylsilanediyl[bis(pentafluorophenyl)(2-methyl-4,5-benzindenylidene)borane](2-methyl-4,5-benzindenyl)dimethylzirconium, methylphenylsilanediyl[bis(pentafluorophenyl)(2-ethyl-4-phenyl-indenylidene)borane](2-ethyl-4-phenylindenyl)dimethylzirconium, ethylene[bis(pentafluorophenyl)(2-methylindenylidene)borane](2-methylindenyl)dimethylzirconium, [bis(pentafluorophenyl)(2-methylbenzindenylidene)borane](2-methylbenzindenyl)diphenylzirconium, dimethylsilanediyl[bis(pentafluorophenyl)(2-methylindenylidene)borane](2-methylindenyl)diphenylzirconium, dimethylsilanediyl[bis(pentafluorophenyl)(2-methylbenzindenylidene)borane](2-methyl-4-phenylindenyl)diphenylzirconium, dimethylsilanediyl[bis(pentafluorophenyl)(2-methyl-4-naphthylindenylidene)borane](2-methyl-4-naphthylindenyl)diphenylzirconium, isopropylidene[bis(pentafluorophenyl)(cyclopentadienylidene)borane](fluorenyl)diphenylzirconium, dimethylsilanediyl[bis(trifluoromethyl)(2-methylbenzindenylidene)borane](2-methylbenzindenyl)diphenylzirconium, dimethylsilanediyl[bis(trifluoromethyl)(2-methyl-4-phenylindenylidene)borane](2-methyl-4-phenylindenyl)diphenylzirconium, dimethylsilanediyl[bis(trifluoromethyl)(2-methyl-4,6-diisopropylindenylidene)borane](2-methyl-4,6-diisopropylindenyl)diphenylzirconium, methylphenylmethylene[bis(pentafluorophenyl)(cyclopentadienylidene)borane](fluorenyl)diphenylzirconium, methylphenylsilanediyl[bis(pentafluorophenyl)(2-methyl-4,5-benzindenylidene)borane](2-methyl-4,5-benzindenyl)diphenyizirconium, methylphenylsilanediyl[bis(pentafluorophenyl)(2-ethyl-4-phenyl-indenylidene)borane](2-ethyl-4-phenylindenyl)diphenylzirconium and ethylene[bis(pentafluorophenyl)(2-methylindenylidene)borane](2-methylindenyl)diphenylzirconium.

14. A catalyst comprising at least one transition metal compound as claimed in claim 1.

15. A catalyst as claimed in claim 14, additionally containing a support.

16. A catalyst as claimed in claim 14, in prepolymerized form.

17. A process for preparing a polyolefin by polymerization of one or more olefins in the presence of a catalyst as claimed in claim 14.

18. The process as claimed in claim 17, wherein one or more olefins of the formula $R^a$—CH=CHR$^b$ are polymerized, $R^a$ and $R^b$ are identical or different and are each a hydrogen atom or a carbon-containing radical having from 1 to 20 carbon atoms, and $R^a$ and $R^b$ together with the atoms connecting them can form one or more rings.

19. The process as claimed in claim 17, wherein one or more 1-olefins of the formula $R^a$—CH=CH—$R^6$, where $R^a$ and $R^b$ are identical or different and are each a hydrogen atom or a carbon radical containing from 1 to 40 carbon atoms or $R^a$ and $R^b$ together with the atoms connecting them form one or more rings are polymerized.

* * * * *